United States Patent
Vu et al.

(10) Patent No.: US 9,223,039 B2
(45) Date of Patent: Dec. 29, 2015

(54) SYSTEM AND METHOD FOR GENERATING MICRO-SEISMIC EVENTS AND CHARACTERIZING PROPERTIES OF A MEDIUM WITH NON-LINEAR ACOUSTIC INTERACTIONS

(75) Inventors: Cung Khac Vu, Houston, TX (US); Kurt Nihei, Oakland, CA (US); Paul A. Johnson, Santa Fe, NM (US); Robert Guyer, Reno, NV (US); James A. Ten Cate, Los Alamos, NM (US); Pierre-Yves Le Bas, Los Alamos, NM (US); Carène S. Larmat, Los Alamos, NM (US)

(73) Assignees: CHEVRON U.S.A. INC., San Ramon, CA (US); LOS ALAMOS NATIONAL SECURITY LLC, Los Alamos, NM (US)

( * ) Notice: Subject to any disclaimer, the term of this patent is extended or adjusted under 35 U.S.C. 154(b) by 1032 days.

(21) Appl. No.: 13/292,948

(22) Filed: Nov. 9, 2011

(65) Prior Publication Data

US 2012/0123684 A1    May 17, 2012

Related U.S. Application Data

(60) Provisional application No. 61/413,173, filed on Nov. 12, 2010.

(51) Int. Cl.
*G01V 1/00* (2006.01)
*G01V 1/44* (2006.01)
(Continued)

(52) U.S. Cl.
CPC    *G01V 1/006* (2013.01); *G01V 1/44* (2013.01); *G01V 1/46* (2013.01); *G01V 1/50* (2013.01);
(Continued)

(58) Field of Classification Search
CPC .................................. G10K 15/02; G01V 1/50
USPC ........................................................... 702/14
See application file for complete search history.

(56) References Cited

U.S. PATENT DOCUMENTS

| | | |
|---|---|---|
| 3,302,745 A | 2/1967 | Ikrath |
| 3,521,154 A | 7/1970 | Maricelli |

(Continued)

FOREIGN PATENT DOCUMENTS

| | | | |
|---|---|---|---|
| CA | 2892437 A1 * | 6/2014 | ............. G01V 1/006 |
| EP | 0 519 810 A1 | 12/1992 | |

(Continued)

OTHER PUBLICATIONS

U.S. Notice of Allowance dated Aug. 18, 20014 for U.S. Appl. No. 13/292,915.

(Continued)

*Primary Examiner* — Sujoy Kundu
*Assistant Examiner* — Steven J Malone
(74) *Attorney, Agent, or Firm* — Pillsbury Winthrop Shaw Pittman, LLP

(57) ABSTRACT

A method and system includes generating a first coded acoustic signal including pulses each having a modulated signal at a central frequency; and a second coded acoustic signal each pulse of which includes a modulated signal a central frequency of which is a fraction d of the central frequency of the modulated signal for the corresponding pulse in the first plurality of pulses. A receiver detects a third signal generated by a non-linear mixing process in the mixing zone and the signal is processed to extract the third signal to obtain an emulated micro-seismic event signal occurring at the mixing zone; and to characterize properties of the medium or creating a 3D image of the properties of the medium, or both, based on the emulated micro-seismic event signal.

35 Claims, 11 Drawing Sheets

(51) Int. Cl.
*G01V 1/50* (2006.01)
*G01V 1/46* (2006.01)
*G10K 15/02* (2006.01)
*G01V 1/52* (2006.01)

(52) U.S. Cl.
CPC ............. *G01V 1/52* (2013.01); *G01V 2210/125* (2013.01); *G01V 2210/127* (2013.01); *G01V 2210/588* (2013.01); *G10K 15/02* (2013.01)

(56) References Cited

U.S. PATENT DOCUMENTS

| | | |
|---|---|---|
| 3,732,945 A | 5/1973 | Lavigne |
| 3,872,421 A | 3/1975 | Rogers et al. |
| 3,974,476 A | 8/1976 | Cowles |
| 4,253,166 A | 2/1981 | Johnson |
| 4,382,290 A | 5/1983 | Havira |
| 4,509,149 A | 4/1985 | Ruehle |
| 4,606,014 A | 8/1986 | Winbow et al. |
| 4,646,565 A | 3/1987 | Siegfried |
| 4,757,873 A | 7/1988 | Linyaev et al. |
| 4,805,873 A | 2/1989 | Mouton |
| 4,885,723 A | 12/1989 | Havira |
| 5,144,590 A | 9/1992 | Chon |
| 5,226,018 A | 7/1993 | Chang et al. |
| 5,521,882 A * | 5/1996 | D'Angelo ................ G01V 1/52 324/335 |
| 5,712,829 A * | 1/1998 | Tang ........................ G01V 1/52 367/25 |
| 5,719,823 A | 2/1998 | Earp |
| 6,009,043 A | 12/1999 | Chon et al. |
| 6,023,443 A * | 2/2000 | Dubinsky ................ E21B 43/08 175/45 |
| 6,175,536 B1 | 1/2001 | Khan |
| 6,216,540 B1 | 4/2001 | Nelson et al. |
| 6,289,284 B1 | 9/2001 | Yamamoto |
| 6,418,081 B1 * | 7/2002 | Sen ........................ F41H 11/12 181/101 |
| 6,427,124 B1 * | 7/2002 | Dubinsky ................ E21B 43/08 702/9 |
| 6,440,075 B1 | 8/2002 | Averkiou |
| 6,466,873 B2 * | 10/2002 | Ren ........................ G01V 1/28 367/51 |
| 6,597,632 B2 | 7/2003 | Khan |
| 6,631,783 B2 | 10/2003 | Khan |
| 6,704,247 B1 | 3/2004 | Ruffa |
| 6,842,400 B2 * | 1/2005 | Blanch .................... G01V 1/50 367/25 |
| 6,865,489 B2 * | 3/2005 | Jing ........................ G01V 1/28 367/73 |
| 6,937,938 B2 | 8/2005 | Sansone |
| 7,035,165 B2 * | 4/2006 | Tang ........................ G01V 1/44 367/25 |
| 7,059,404 B2 | 6/2006 | Flecker et al. |
| 7,301,852 B2 | 11/2007 | Leggett, III et al. |
| 7,310,580 B2 | 12/2007 | Zhou et al. |
| 7,319,639 B2 * | 1/2008 | Heyman ................. G01V 1/001 367/92 |
| 7,463,551 B2 | 12/2008 | Leggett, III et al. |
| 7,535,795 B2 | 5/2009 | Varsamis et al. |
| 7,652,951 B2 | 1/2010 | Leggett et al. |
| 7,675,815 B2 * | 3/2010 | Saenger ................. G01V 1/28 367/38 |
| 7,710,822 B2 | 5/2010 | Harmon |
| 7,907,474 B2 * | 3/2011 | Scott et al. ........................ 367/32 |
| 7,966,874 B2 * | 6/2011 | Hassan ................. E21B 47/091 702/9 |
| 8,116,167 B2 | 2/2012 | Johnson et al. |
| 8,186,432 B2 * | 5/2012 | Freeman ................. G01V 1/40 166/250.14 |
| 8,576,659 B2 | 11/2013 | Egerev et al. |
| 2002/0134612 A1 * | 9/2002 | Khan ........................ G01V 1/006 181/108 |
| 2004/0095847 A1 | 5/2004 | Hassan et al. |
| 2005/0036403 A1 * | 2/2005 | Leggett, III .............. G01V 1/44 367/32 |
| 2006/0056468 A1 * | 3/2006 | Dantus .................... G01J 11/00 372/28 |
| 2009/0067285 A1 * | 3/2009 | Robertsson .......... G01V 1/3808 367/24 |
| 2009/0086574 A1 * | 4/2009 | Scott ....................... G01V 1/005 367/25 |
| 2009/0308163 A1 | 12/2009 | Fukutomi et al. |
| 2009/0310441 A1 * | 12/2009 | Johnson ................. G01V 1/46 367/35 |
| 2010/0002540 A1 * | 1/2010 | Vu ........................... G01V 1/46 367/25 |
| 2010/0036244 A1 * | 2/2010 | Angelsen ................ A61B 8/08 600/438 |
| 2010/0110831 A1 * | 5/2010 | Love ....................... G01V 1/005 367/32 |
| 2010/0265794 A1 * | 10/2010 | Johnson ................. G01V 1/44 367/32 |
| 2010/0284250 A1 | 11/2010 | Cornish et al. |
| 2011/0163733 A1 * | 7/2011 | Nelson, Jr. ............. G01V 3/082 324/72 |
| 2011/0246140 A1 * | 10/2011 | Abubakar ................ G01V 1/28 703/2 |
| 2012/0062408 A1 * | 3/2012 | Bausov .................... G01V 3/12 342/22 |
| 2012/0095699 A1 * | 4/2012 | Angelsen ............. G01S 7/52038 702/33 |
| 2012/0123684 A1 * | 5/2012 | Vu ........................... G01V 1/46 702/14 |
| 2014/0043938 A1 * | 2/2014 | Sinha ....................... G01V 1/50 367/31 |
| 2014/0204700 A1 * | 7/2014 | Valero ..................... G01V 1/48 367/7 |
| 2015/0084782 A1 * | 3/2015 | Zhang ..................... G01V 1/36 340/853.2 |

FOREIGN PATENT DOCUMENTS

| | | | |
|---|---|---|---|
| EP | 1122558 A | 8/2001 | |
| GB | 2168568 | 6/1986 | |
| GB | 2404983 A | 2/2005 | |
| JP | 07-151863 | 6/1995 | |
| SU | 913303 | 3/1982 | |
| WO | WO 0101350 A1 * | 1/2001 | ............... G01V 1/34 |
| WO | 0194983 A2 | 12/2001 | |
| WO | WO 02/04985 A2 | 1/2002 | |
| WO | WO 2007/030016 | 3/2007 | |
| WO | WO 2008/094050 A2 | 8/2008 | |
| WO | WO 2010-121202 | 10/2010 | |

OTHER PUBLICATIONS

Mexican Office Action dated Jun. 5, 2014 for Appln. No. MX/A/2013/005333.
U.S. Notice of Allowance dated Sep. 5, 20014 for U.S. Appl. No. 13/292,924.
U.S. Office Action dated Aug. 25, 2014 for U.S. Appl. No. 13/292,908.
Australian Office Action dated Aug. 28, 2014 for Appln. No. 2011326570.
Peter J. Westervelt; "Parametric Acoustic Array", The Journal of the Acoustical Society of America, vol. 35, No. 4, Apr. 1963, pp. 535-537.
International Search Report and Written Opinion for PCT International Patent Application No. PCT/US2009/047934, mailed Jan. 12, 2009.
Johnson et al., "Nonlinear Generation of Elastic waves in Crystalline Rock", Journal of Geophysical Research, vol. 92, No. B5, pp. 3597-3602, Apr. 10, 1987.
International Search Report and Written Opinion for PCT International Patent Application No. PCT/US2009/047184, mailed Dec. 21, 2009.
International Preliminary Report on Patentability for PCT International Patent Application No. PCT/US2009/047184, mailed Dec. 23, 2010.
International Search Report and Written Opinion for PCT International Patent Application No. PCT/US2010/031485, mailed Aug. 2, 2010.

(56) References Cited

OTHER PUBLICATIONS

International Search Report and Written Opinion for PCT International Patent Application No. PCT/US2010/031490, mailed Sep. 14, 2010.
Aas et al.; 3-D Acoustic Scanner, SPE, Society of Petroleum Engineers, Sep. 23-26, 1990, pp. 725-732.
Ostrovsky. L.A., and Johnson, P.A., "Dynamic Nonlinear Elasticity in Geomaterials", Rivista del Nuovo Cimento, vol. 24, No. 7., 2001.
Johnson, Paul A., and Shankland, Thomas J., "Nonlinear Generation of Elastic Waves in Granite and Sandstone: Continuous Wave and Travel Time Observations", Journal of Geophysical Research, vol. 94, No. B12, 1989, pp. 17,729-17,733.
Jones, G.L. and Kobett, D.R., "Interaction of Elastic Waves in an Isotropic Solid", The Journal of the Acoustical Society of America, vol. 35, No. 1, 1963, pp. 5-10.
Rollins, F.R., Taylor, L.H. and Todd, P.H., "Ultrasonic Study of Three-Phonon Interactions. II. Experimental Results", Physical. Review, vol. 136, No. 3A, 1964, pp. 597-601.
Korneev, Valeri A., Nihei, Kurt T. and Myer, Larry R., "Nonlinear Interaction of Plane Elastic Waves", Lawrence Berkeley National Laboratory Report LBNL-41914, 1998.
International Preliminary Report on Patentability for PCT International Patent Application No. PCT/US2010/031490, mailed Oct. 27, 2011.
International Preliminary Report on Patentability for PCT International Patent Application No. PCT/US2010/031485, mailed Oct. 27, 2011.
Tserkovnyak et al.; "Non-linear tube waves in permeable formations: Difference frequency generation", Journal of the Acoustical Society of America, Jul. 1, 2004, vol. 116, Issue 1, pp. 209-216.
Singapore Office Action for Appln. No. 201009640-2, mailed Dec. 2, 2011.
PCT International Search Report and Written Opinion for PCT International Patent Application No. PCT/US2011/035608, mailed Dec. 22, 2011.
PCT International Search Report and Written Opinion for PCT International Patent Application No. PCT/US2011/035595, mailed Dec. 27, 2011.
PCT International Search Report and Written Opinion for PCT International Patent Application No. PCT/US2011/035358, mailed Dec. 29, 2011.
International Preliminary Report on Patentability for PCT International Patent Application No. PCT/US2009/047934, mailed Jan. 13, 2011.
International Preliminary Report on Patentability for PCT International Patent Application No. PCT/US2009/047184, mailed Dec. 14, 2010.
International Preliminary Report on Patentability for PCT International Patent Application No. PCT/US2009/047934, mailed Dec. 1, 2009.
U.S. Office Action dated Dec. 8, 2014 for U.S. Appl. No. 13/292,935.
U.S. Office Action dated Nov. 26, 2014 for U.S. Appl. No. 13/292,941.
Mexican Office Action dated Sep. 25, 2014 for Appln. No. MX/a/2014/005694.
U.S. Office Action dated Feb. 3, 2015 for U.S. Appl. No. 13/292,908.
Singapore Search Report and Written Opinion mailed Dec. 26, 2014 for Appln. No. 2013036405.
Chinese Office Action dated Jul. 20, 2015 for Appln. No. 201180062766.7.
Eurasian Patent Office (EAPO) dated Aug. 11, 2015 for Appln. No. 201390693.
European Office Action dated Jul. 17, 2015 for Appln. No. 11791670.0.
Johnson P A et al: "Continuous Wave Phase Detection for Probing Nonlinear Elastic Wave Interactions in Rocks", TheJournal of the Acoustical Society of America, American Institute of Physics forthe Acoustical Society of America, New York, NY, US, vol. 89, No. 2. Feb. 1, 1991pp. 598-603.
Patent Examination Report dated Mar. 30, 2015 for corresponding Australian Patent Application No. 2011326570 (2 pages).
Chinese Office Action dated Apr. 28, 2015 for corresponding Chinese Patent Application No. 201180061262.3 (11 pages).
U.S. Office Action dated May 1, 2015 for corresponding U.S. Appl. No. 13/292,908 (10 pages).
Mexican Office Action dated May 13, 2015 for Appln. No. MX/a/2014/014944.
US Office Action dated Sep. 16, 2015 for U.S. Appl. No. 13/292,908.
Japanese Office Action dated Sep. 30, 2015 for Appln. No. 2013-538852.
Chinese Office Action dated Oct. 20, 2015 for Appln. No. 201180061262.3.

\* cited by examiner

SYSTEM AND METHOD FOR GENERATING MICRO-SEISMIC EVENTS AND CHARACTERIZING PROPERTIES OF A MEDIUM WITH NON-LINEAR ACOUSTIC INTERACTIONS

STATEMENT REGARDING GOVERNMENT RIGHTS

The United States government has rights in this invention pursuant to Contract No. DE-AC52-06NA25396 between the United States Department of Energy and Los Alamos National Security, LLC for the operation of Los Alamos National Laboratory.

CROSS REFERENCE TO RELATED APPLICATION

This application claims the benefit of U.S. patent application Ser. No. 61/413,173, filed on Nov. 12, 2010, the entire contents of which is incorporated herein by reference.

FIELD

The present invention relates to methods and systems for generating micro-seismic events within a target volume of a medium and generating non-linear acoustic interaction signals in the medium to characterize properties of the medium.

BACKGROUND

Conventional methods and systems for interrogating a material or medium are generally based on linear interaction of acoustic waves with the material or medium. Some methods and techniques in the geophysics community have been implemented to study non-linear interaction of acoustic waves in a rock formation but each has its own limitations. The time reversal technique involving the propagation backward in time of a wavefield scattered by linear interaction in a medium has also been used to focus the wavefield back onto a point in the medium that acts as a micro-seismic source.

Therefore, there remains a need for methods and systems for investigating non-linear properties of materials that provide enhanced multi-dimensional image information of non-linear properties of the material or medium using non-linear acoustic interactions in the medium to emulate micro-seismic sources originating from locations of the non-linear interaction in the medium.

SUMMARY

An aspect of the present disclosure is to provide a method of generating a micro-seismic event in a medium from a non-linear interaction to characterize the medium. The method includes generating, by a first acoustic source, a first coded acoustic signal comprising a first plurality of pulses arranged as a time sequence, the first plurality of pulses being separated in time, each pulse comprising a modulated signal at a central frequency, wherein central frequencies of two consecutive pulses are different; generating, by a second acoustic source, a second coded acoustic signal comprising a second plurality of pulses arranged as a time sequence, the second plurality of pulses being separated in time, wherein a separation in time between centers of two consecutive pulses is the same as a separation in time between centers of two corresponding pulses in the first plurality of pulses, wherein a start time difference is provided between a start time of a broadcast of the second plurality of pulses and a start time of a broadcast of the first plurality of pulses, wherein each pulse comprises a modulated signal and a central frequency of the modulated signal within each pulse in the second plurality of pulses is a selected fraction d of the central frequency of the modulated signal for the corresponding pulse in the first plurality of pulses; wherein the first acoustic source and the second acoustic source are controllable such that trajectories of the first and the second acoustic signals intersect in a mixing zone within the medium. The method further includes receiving, by a receiver, a detected signal including a third signal being generated by a non-linear mixing process from the first acoustic signal and the second acoustic signal in the mixing zone; performing, by a processor, data processing on the received signal, or correlating with a coded signal template, or both, to extract the third signal generated by the non-linear mixing process over noise or over signals generated by a linear interaction process, or both, to obtain an emulated micro-seismic event signal occurring at the mixing zone; and characterizing properties of the medium or creating a 3D image of the properties of the medium, or both, based on the emulated micro-seismic event signal.

Another aspect of the present disclosure is to provide a system for generating a micro-seismic event in a medium from a non-linear interaction to characterize the medium. The system includes a first acoustic source configured to generate a first coded acoustic signal comprising a first plurality of pulses arranged as a time sequence, the first plurality of pulses being separated in time, each pulse comprising a modulated signal at a central frequency, wherein central frequencies of two consecutive pulses are different; and a second acoustic source configured to generate a second coded acoustic signal comprising a second plurality of pulses arranged as a time sequence, the second plurality of pulses being separated in time, wherein a separation in time between centers of two consecutive pulses is the same as a separation in time between centers of two corresponding pulses in the first plurality of pulses, wherein a start time difference is provided between a start time of a broadcast of the second plurality of pulses and a start time of a broadcast of the first plurality of pulses, wherein each pulse comprises a modulated signal and a central frequency of the modulated signal within each pulse in the second plurality of pulses is a selected fraction d of the central frequency of the modulated signal for the corresponding pulse in the first plurality of pulses. The first acoustic source and the second acoustic source are controllable such that trajectories of the first and the second acoustic signals intersect in a mixing zone within the medium. The system also includes a receiver configured to receive a detected signal including a third signal being generated by a non-linear mixing process from the first acoustic signal and the second acoustic signal in the mixing zone. The system further includes a processor configured to perform data processing on the received signal, or correlate with a coded signal template, or both, to extract the third signal generated by the non-linear mixing process over noise or over signals generated by a linear interaction process, or both, to obtain an emulated micro-seismic event signal occurring at the mixing zone of the first and second acoustic signals so as to characterize properties of the medium or create a 3D image of the properties of the medium, or both, based on the emulated micro-seismic event signal.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various Figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

According to some aspects of the present invention, a basic remote sensing system with non-linear acoustic probes generally includes two acoustic sources S1 and S2 located at two spatially separate positions and an acoustic detector or an array of acoustic detectors at different locations. The two acoustic sources S1 and S2 are configured to generate primary acoustic waves or acoustic beams that intersect at various locations in the medium to be investigated. The detector or detectors are configured to receive a third acoustic wave generated by the interaction of the two primary acoustic waves with a non-linearity of the medium. The interaction volume can then be considered as the source of the third acoustic wave. The two primary waves can be either compressional or shear acoustic waves or acoustic beams. In the present disclosure, the term "acoustic" can refer to P, SV or SH acoustic mode.

In one embodiment, it is possible to code the acoustic signals from acoustic sources S1 and S2, detect the non-linear response of the medium and process the detected non-linear signal on a computer to generate a band-limited spike acoustic signal that emulates a micro-seismic event occurring at the non-linear interaction mixing zone of the coded acoustic waves from acoustic sources S1 and S2 in the medium. This band-limited spike acoustic signal is referred to herein as the emulated micro-seismic event originating from the non-linear interaction. Various embodiments of the present disclosure describe a method and a system to:

a) set up suitable measurement configuration of sources and receivers to probe the medium remotely and to detect the non-linear response of the medium;

b) code the source signals;

c) process the coded detected signals on a processor to generate measurement responses at detectors or receivers that correspond to emulated micro-seismic events at specific locations in the medium for which the strengths of the events are proportional to the non-linear properties of the medium; and d) process the emulated micro-seismic events to generate three dimensional (3D) images of the non-linear properties and the propagation velocity model of the medium.

As discussed in the U.S. Patent Application Publication No. US2010/0265795 A1 entitled "SYSTEM AND METHOD TO CREATE THREE-DIMENSIONAL IMAGES OF NON-LINEAR ACOUSTIC PROPERTIES IN THE REGION REMOTE FROM THE BOREHOLE", the non-linear interaction between two primary acoustic waves to generate a third wave is governed by specific selection rules for various primary acoustic waves P, SV or SH. One particular mode of non-linear interaction is P+P→SV. This mode will be used as an example to explain various embodiments of the present disclosure. However, any other mode of non-linear interactions of P, SV or SH waves can equally be used.

Figure 1:
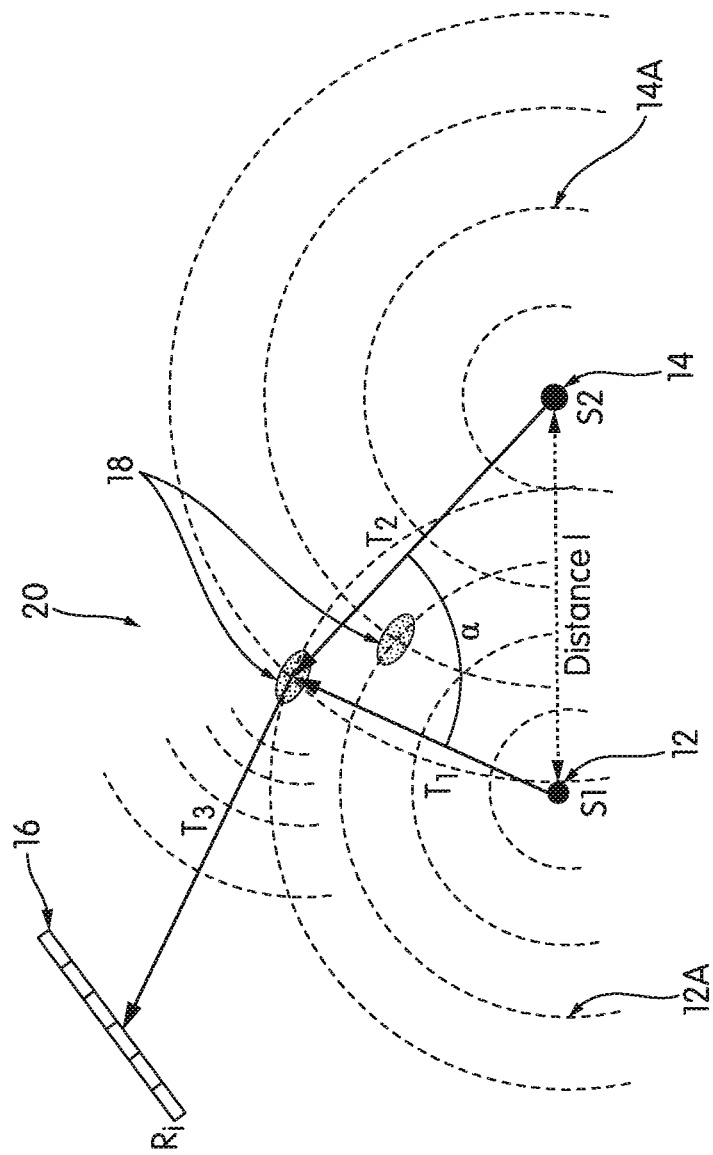
FIG. 1 is a schematic representation of remote sensing system acoustic probes to generate non-linear interaction in a medium, according to an embodiment of the present invention.

FIG. 1 is a schematic representation of remote sensing system acoustic probes to generate non-linear interaction in a medium, according to an embodiment of the present invention. The remote sensing system 10 comprises a first acoustic source 12 and a second acoustic source 14. The first acoustic source (S1) 12 and the second acoustic source (S2) 14 are separated by distance 1. The remote sensing system further comprises an array of acoustic detectors 16 which are positioned at different locations with respect to first acoustic source 12 and second acoustic source 14. Although an array of acoustic detectors 16 is shown in FIG. 1, one or more detectors can be used. The array of acoustic detectors 16 can be moved to different locations. The first source 12 and the second source 14 are configured to generate acoustic waves or acoustic beam probes 12A and 14A, respectively. The waves 12A and 14A intersect at various locations 18 of medium 20 to be investigated. A third wave 16A can be generated by the non-linearity of the medium 20 at the intersection loci 18 of acoustic waves 12A and 14A.

In one embodiment, the first acoustic sources (S1) 12 and (S2) 14 are configured to generate coded acoustic signals. A coding scheme can be selected so as to achieve desired mixing characteristics within the medium.

In one embodiment, the coded signals for the two primary acoustic waves 12A and 14A can mix in the medium 20 and generate by non-linear interaction an inherited specific coded signal for the third acoustic wave 16A. The measurement of the coded returning signal 16A from the non-linear interaction in the medium 20 can be correlated with a template coded signal which can be computed from the selection rules of non-linear mixing in the region where the mixing occurs. An example of such technique can be found in U.S. Application entitled "SYSTEM AND METHOD FOR INVESTIGATING SUB-SURFACE FEATURES OF A ROCK FORMATION WITH ACOUSTIC SOURCES GENERATING CODED SIGNALS," which is filed concurrently with the present application, the entire contents of which is incorporated herein by reference.

For example, given an appropriate start time difference δ between primary coded acoustic signals within acoustic waves 12A and 14A and given a frequency ratio between the frequencies of the coded acoustic signals within acoustic waves 12A and 14A, the resulting signal generated from each zone of non-linear interaction corresponds to the third acoustic wave 16A. The third acoustic wave 16A can be decoded, for example, by a correlation processing technique to isolate or find an acoustic pulse signal originating from or generated by the non-linear interaction. The decoded acoustic pulse signal can be considered as a frequency band-limited acoustic signal generated by an emulated micro-seismic event generated at the intersection of the wavefronts of the two primary waves 12A and 14A. The strength of the pulse is proportional to the non-linear properties of the zones of interaction 18 and the product of strain amplitudes of the primary waves 12A and 14A. A travel time to the receivers 16 corresponds to a sum of travel time from the acoustic source 12 or acoustic source 14 to a locus of the zone of non-linear interaction and a travel time of the third wave 16A from the locus of interaction 18 to receiver 16.

Figure 2:
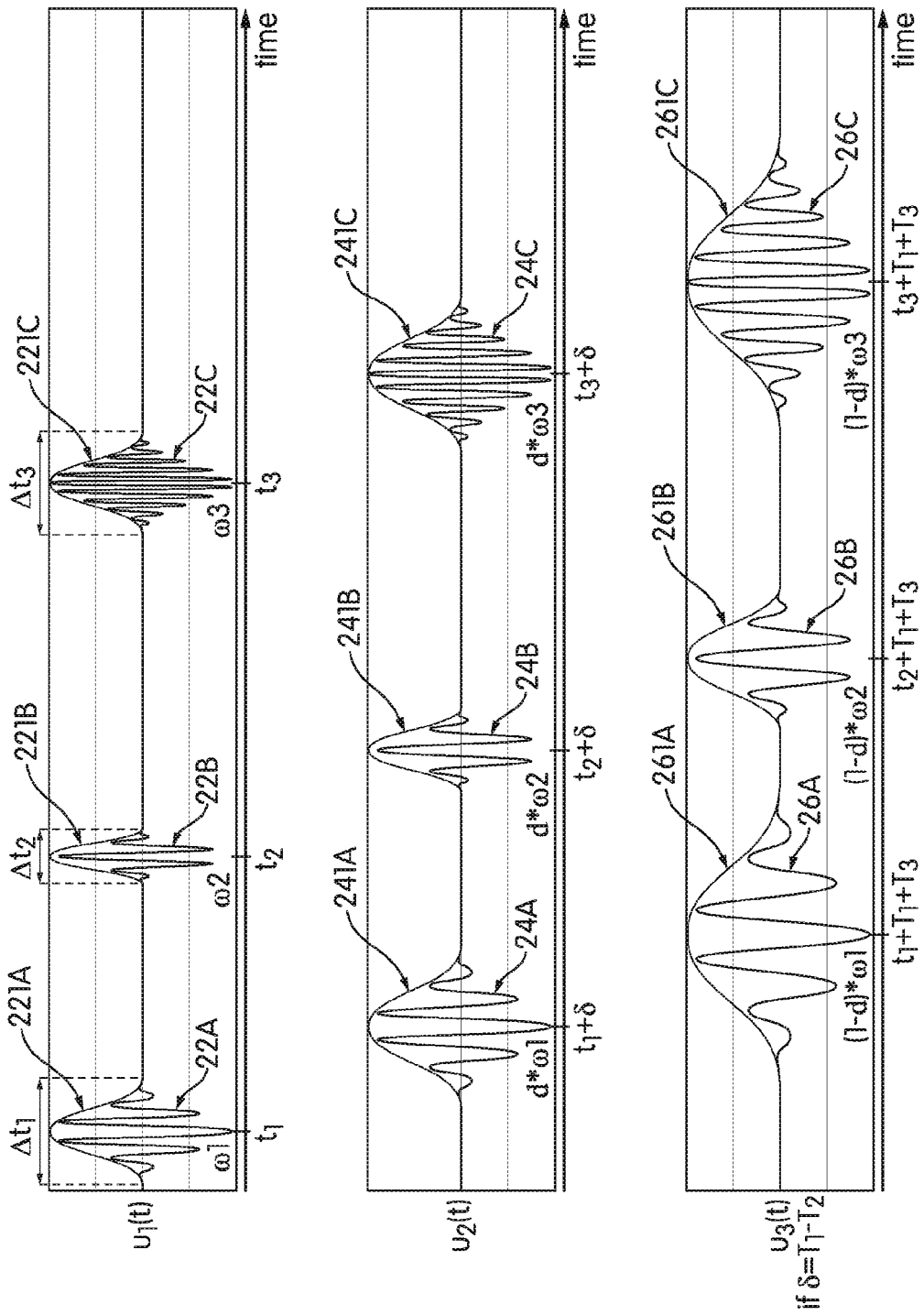
FIG. 2 shows a first acoustic signal generated by the first source, a second signal acoustic signal generated by second source and a third acoustic signal which results from a non-linear mixing of the first acoustic signal and the second acoustic signal in a non-linear mixing zone, according to an embodiment of the present invention.

FIG. 2 shows a first acoustic signal $u_1$ generated by the first source S1, a second signal acoustic signal $u_2$ generated by second source S2 and a third acoustic signal $u_3$ which results from a non-linear mixing of the first acoustic signal $u_1$ and the second acoustic signal $u_2$ in a non-linear mixing zone, according to an embodiment of the present invention.

In one embodiment, the first acoustic source Si broadcasts a compressional (P) wave (e.g., a plane wave or a beam wave) with the $u_1$ signal comprising a plurality or train of pulses of acoustic signals. In one embodiment, the plurality of acoustic pulses are spaced apart in time such that there is no overlap of pulses. Each pulse has a modulated acoustic signal at a central frequency $\omega_m$, where m=1 through M and M is the number of pulses in the first plurality of pulses. Each acoustic pulse has an amplitude envelope with a given time duration. The broadcast central frequencies $\omega_m$ are staged sequentially at fixed time intervals during the entire signal broadcast.

The second acoustic source S2 broadcasts a compressional (P) wave (e.g., a plane wave or a beam) with the $u_2$ signal comprising a plurality or train of pulses of acoustic signals. The second plurality of acoustic pulses of $u_2$ signal have the same time spacing between centers of the pulses as the time spacing between centers of the pulses in the first plurality of pulses of $u_1$ signal. Each pulse has a modulated acoustic signal at a central frequency ($d*\omega_m$) where m=1 through M and M is the number of pulses in the first plurality of pulses and d is a fixed frequency ratio for all the pulses. Each acoustic pulse has an amplitude envelope with a time duration. As it can be appreciated, the symbol "*" is used herein as a multiplication operator.

An embodiment of the broadcast coded signals is shown in FIG. 2 in which first three pulses of the plurality of pulses of $u_1$ signal are shown. The first acoustic signal $u_1$ is depicted as having a first pulse 22A, a second pulse 22B and a third pulse 22C. The first pulse 22A is generated at time $t_1$. The first pulse has a time width or time duration $\Delta t_1$. The first pulse 22A has a first envelope 221A and a first modulated signal therein having a first central frequency $\omega_1$. The second pulse 22B is generated at time $t_2$. The second pulse has a time width or time duration $\Delta t_2$. The second pulse 22B has a second envelope 221B and a second modulated signal therein having a second central frequency. $\omega_2$. The third pulse 22C is generated at time $t_3$. The third pulse has a time width or time duration $\Delta t_3$. The third pulse 22C has a third envelope 221C and a third modulated signal therein having a third central frequency $\omega_3$. In one embodiment, for example as shown in FIG. 2, the first envelope of the first pulse, the second envelope of the second pulse and the third envelope of the third pulse are different. In one embodiment, the first frequency $\omega_1$, the second frequency $\omega_2$ and the third central frequency $\omega_3$ are different. However, envelopes of pulses 22A, 22B and 22C can be the same. The first plurality of pulses 22A, 22B and 22C are separated in time (t1 is different from t2 which is different from t3). In addition, central frequencies (e.g., ω1 and ω2) of two consecutive pulses 22A and 22B, for example, are different. Although, the first signal $u_1$ is depicted in FIG. 2 as having 3 pulses, as it can be appreciated the first acoustic signal $u_1$ can have one or more pulses (i.e., m is equal 1 to M pulses, where M is an integer number equal to or greater than 1).

The second compressional acoustic source broadcast acoustic signals of many frequencies ($d*\omega_m$), where d is a fixed frequency ratio for all values of m with an amplitude envelope and the frequencies sequentially at the same fixed time intervals as the first acoustic signal u1. For example, as shown in FIG. 2, the second acoustic signal is depicted as having a first acoustic pulse 24A, a second acoustic pulse 24B and a third acoustic pulse 24C. The first pulse 24A is generated at time ($t_1+\delta$), where δ is the start time difference between the generation of the first acoustic signal and the second acoustic signal. In other words, δ corresponds to a start time difference provided between a start time of a broadcast of the first plurality of pulses 22A, 22B and 22C and a start time of a broadcast of the second plurality of pulses 24A, 24B and 24C. The first acoustic pulse 24A has a first envelope 241A and a first modulated signal therein having first central frequency ($d*\omega_1$), where d is the frequency ratio between the frequencies of the modulated signals within the acoustic pulse 22A, 22B or 22C in the first acoustic signal u1 and the modulated signals within the corresponding acoustic pulse 24A, 24B or 24C, respectively, of the second acoustic signal u2. The second acoustic pulse 22B is generated at time ($t_2+\delta$). The second acoustic pulse 22A has a second envelope 241B and a second modulated signal therein having a second central frequency ($d*\omega_2$). The third acoustic pulse 24C is generated at time ($t_3+\delta$). The third pulse 24C has a third envelope 241C and a third modulated signal therein having a third central frequency ($d*\omega_3$). In one embodiment, for example as shown in FIG. 2, the first envelope of the first acoustic pulse 24A, the second envelope of the second acoustic pulse 24B and the third envelope of the third acoustic pulse 24C are different. However, the envelopes of the pulses 24A, 24B and 24C can also be the same. In one embodiment, the first central frequency ($d*\omega_1$), the second central frequency ($d*\omega_2$), and the third central frequency ($d*\omega_3$) are different. A separation in time between centers of two consecutive pulses (e.g., 24A and 24B) in the second plurality of pulses is the same as a separation in time between centers of two corresponding pulses (22A and 22B) in the first plurality of pulses. In one embodiment, a separation in time between centers of two consecutive pulses (e.g., 22A and 22B) in the first plurality of pulses can be greater than a time duration of each pulse (i.e., greater than time duration $\Delta t_1$ and time duration $\Delta t_2$). Although, the second acoustic signal $u_2$ is depicted in FIG. 2 as having 3 pulses, as it can be appreciated the second acoustic signal $u_2$ can have one or more pulses (i.e., m pulses, where m is an integer equal to or greater than 1).

The acoustic signals $u_1$ and $u_2$ can be represented mathematically by the following relations (1) and (2) respectively.

$$u_1(t) = \sum_m E1_m(t - T_m) * \exp(i\omega_m * (t - T_m)) * \exp(i\zeta_m) \quad (1)$$

and $$u_2(t - \delta) = \sum_m E2_m(t - (T_m + \delta)) * \exp(id * \omega_m * (t - (T_m + \delta))) * \exp(i\zeta_m) \quad (2)$$

where m is a index number associated with a pulse;

$\Sigma$ denotes a summation over index m=1 to M, with M being an integer equal or greater than 1;

$E1_m(t-t_m)$ is an amplitude envelope of pulse m of the first acoustic signal $u_1$;

$E2_m(t-t_m-\delta)$ is an amplitude envelope of pulse m of the second acoustic signal $u_2$;

$\omega_m$ is the central frequency of the modulated signal of pulse m of the first acoustic signal $u_1$;

($d*\omega_m$) is the central frequency of the modulated signal of pulse m of the second acoustic signal $u_2$;

d is a frequency ratio between the frequency $\omega_m$ and frequency $d*\omega_m$, where d is a real positive number;

$\delta$ is the start time difference between the generation of the first acoustic signal $u_1$ and the second acoustic signal $u_2$;

$\exp(i\omega_m(t-t_m))$ is the modulated signal within the pulse m of the first acoustic signal $u_1$;

$\exp(id*\omega_m(t-t_m-\delta))$ is the modulated signal within the pulse m of second acoustic signal u2;

$t_m$ is the time pulse m is generated in the first acoustic signal $u_1$;

$t_m+\delta$ is the time pulse m is generated in the second acoustic signal $u_2$; and $\exp(i\zeta_m)$ is a phase term of each pulse m within the first signal $u_1$ or second signal $u_2$.

In one embodiment, frequencies $\omega_m$ and $\omega_{m+1}$ of two consecutive pulses m and m+1 are selected to be different from each other such that the difference between the frequencies $\omega_m$ and $\omega_{m+1}$ denoted as ($\omega_m-\omega_{m+1}$) is not small compared with $\omega_m$. In one embodiment, the range of frequencies $\omega_m$ is large spanning one or more octaves. In one embodiment, the time separation (t1–t2) between two adjacent time periods t1 and t2 is larger than the time duration $\Delta t_m$ of a pulse m (where m is an integer number equal to or greater than 1). In other words, the time difference ($t_{m+1}-t_m$) between consecutive pulses m and m+1 is greater than $\Delta t_m$ (i.e., $\Delta t_m \ll (t_{m+1}-t_m)$) and the time difference ($t_m-t_{m-1}$) between consecutive pulses m−1 and m is greater than $\Delta t_m$ (i.e., $\Delta t_m \ll (t_m-t_{m-1})$).

When the first acoustic signal $u_1$ and the second acoustic signal $u_2$ non-linearly mix at a certain distance, the non-linear mixing generates a third acoustic signal $u_3$. The third acoustic signal $u_3$ comprises a series of acoustic pulses, each acoustic pulse having an envelope and a modulated signal. For the mth pulse, the modulated signal of the mth pulse in the $u_3$ signal has a central frequency equal to a difference between a frequency $\omega_m$ of a modulated signal of the first acoustic signal and a frequency ($d*\omega_m$) of a modulated signal of the second acoustic signal, i.e., ($\omega_m-d*\omega_m$) or (($1-d)*\omega_m$).

For example, as shown in FIG. 2, the third acoustic signal $u_3$ is depicted as having a first acoustic pulse 26A, a second acoustic pulse 26B and a third acoustic pulse 26C. These pulses 26A, 26B and 26C are generated at the mixing zone when the start time difference $\delta$ between the generation of the first acoustic signal and the generation of the second acoustic signal is equal to the time difference between $T_2$ and $T_1$, where $T_1$ is a travel time of the first acoustic signal $u_1$ from the first acoustic source Si to a center of the mixing zone and $T_2$ is a travel time of the second acoustic signal $u_2$ from the second acoustic source S2 to a center of the mixing zone. The first pulse 26A is received at time $t1+T_1+T_3$, where time $T_3$ is a travel time from the center of the mixing zone where the third signal is generated to the receiver. In one embodiment, a separation in time between centers of two consecutive pulses (e.g., pulses 26A and 26B) is the same as the separation in time between centers of two corresponding consecutive pulses in the first plurality of pulses (22A and 22B).

The first pulse 26A has an envelope 261A and a first modulated signal therein having a first central frequency $(1-d)*\omega_1$. The envelope of pulse 26A is broader than the envelope of pulse 22A in the first signal $u_1$ and pulse 24A in the second signal $u_2$. This first central frequency $(1-d)*\omega_1$ corresponds to a frequency difference between the central frequency $\omega_1$ of the first pulse 22A in the first signal $u_1$ and the central frequency ($d*\omega_1$) of the second pulse 24A in the second signal $u_2$. The second pulse 26B is received at time $t_2+T_1+T_3$. The second pulse 26B has an envelope 261B and a second modulated signal therein having a second central frequency $(1-d)*\omega_2$. The envelope of pulse 26B is broader than the envelope of pulse 22B in the first signal $u_1$ and pulse 24B in the second signal $u_2$. This second central frequency $(1-d)*\omega_2$ corresponds to a frequency difference between a central frequency $\omega_2$ of the second pulse 22B in the first signal u1 and a central frequency ($d*\omega_2$) of the second pulse 24B in the second signal $u_2$. The third pulse 26C is received at time $t_3+T_1+T_3$. The third pulse 26C has an envelope 261C and a third modulated signal therein having a third frequency $(1-d)*\omega_3$. The envelope of pulse 26C is broader than the envelope of the pulse 22C and pulse 24C. This central frequency (131 d)*107 $_3$ corresponds to a frequency difference between a central frequency $\omega_3$ of the third pulse 22C in the first signal $u_1$ and a central frequency ($d*\omega_3$) of the third pulse 24C in the second signal $u_2$. Therefore, an arrival time at the receiver of each pulse (e.g., pulse 26A, 26B or 26C) of the third plurality of pulses is time delayed relative to a generation of a corresponding pulse (22A, 22B or 22C) of the first plurality of pulses by a total of the travel time ($T_1$) from the first acoustic source to a center of the mixing zone and the travel time ($T_3$) from the center of the mixing zone to the receiver.

The third signal $u_3$ generated from a non-linear interaction of the first and second signals within the non-linear medium can be expressed by the following mathematical formula.

$$u_3 \propto \sum_n E3_m(t - (t_m + T_1 + T_3)) * \qquad (3)$$

$$\exp(i*(1-d)*\omega_m*(t-(t_m+T_1+T_3)))*\exp(i\zeta_m)$$

where m is an index number associated with each pulse;

Σ denotes a summation over index m=1 to M with M being an integer equal or greater than 1;

$E3_m(t-t_m-T_1)$ is an amplitude envelope of pulse m of the third signal $u_3$; $E3_m$ is an envelope function that is slightly wider than $E1_m$ and $E2_m$ and can be calculated from $E1_m$ and $E2_m$, $\omega_m$, d and the sizes of the mixing zones;

$(1-d)*\omega_m$ is the central frequency of the modulated signal of pulse m of the third signal $u_3$;

d is a frequency ratio between the frequency $\omega_m$ and frequency $d*\omega_m$, where d is a real positive number;

$\exp(i(1-d)*\omega_m *(t-t_m-T_1-T_3))$ is the modulated signal within the pulse m of third signal u3;

$t_m+T_1+T_3$ is the time pulse m in the third signal $u_3$ is received; and $\exp(i\zeta_m)$ is a phase term of each pulse m within the third signal $u_3$.

In one embodiment, for P+P→SV, if α is the angle between the wavefront of first signal 12A and the wavefront of the second signal 14A in the non-linear mixing zone, as shown in FIG. 1, selection rules of non-linear interaction of acoustic waves dictate that there will be a specific frequency ratio d between the two primary frequencies $\omega_m$ and $(d*\omega_m)$ (for example, $\omega_1$ and $d*\omega_1$) for which a third wave of a frequency equal to the difference of the primary frequencies $\omega_m$ and $(d*\omega_m)$ can be generated. Given an intersecting angle α between wavefronts of first acoustic signal $u_1$ and second acoustic signal $u_2$, d satisfies the following equation (4).

$$\sin(\alpha/2) = (1-d)\sqrt{(V_p/V_s)^2 - 1}/(2\sqrt{d}) \qquad (4)$$

where Vp and Vs are the compressional wave velocity and shear wave velocity at the mixing zone.

In one embodiment, when $T_1-T_2=\delta$ (i.e., when the time difference $T_1-T_2$ between a travel time $T_1$ of a pulse m of the first acoustic signal u1 to a center of the mixing zone and a travel time $T_2$ of a pulse m of the second acoustic signal $u_2$ from the second acoustic source S2 to a center of the mixing zone is equal to start time difference δ between the generation of the pulse m of the first acoustic signal $u_1$ and the pulse m of the second acoustic signal $u_2$) and frequency ratio between the frequency $\omega_m$ of the modulated signal within a pulse m of the first acoustic signal and frequency $d\omega_m$ of the modulated signal within a pulse m of the second acoustic signal satisfies equation (4), there is complete alignment of all the pulses of the two coded broadcast signals $u_1$ and $u_2$ to generate the third wave $u_3$ with the coded signal as shown in FIG. 2. It can be shown that, in the absence of strong absorption Q propagation effect, the third wave is an effective broadcast from the center of the mixing zone $M_c$ with the following inherited coded signal $u_3$ of equation (3).

For example, if $E1_m(t)$ and $E2_m(t)$ are chosen to be Gaussian functions then the amplitude of the envelope $E1_m(t-t_m)$ and $E2_m(t-t_m)$ of pulse m of the first acoustic signal $u_1$ can be expressed by equation (5).

$$E1_m(t-t_m) = E2_m(t-t_m) = \exp(-(t-t_m)^2/4(\Delta t_m)^2) \qquad (5)$$

and the amplitude of the envelope $E3_m(t-t_m)$ can be expressed by equation (6).

$$E3_m(t-t_m) = \exp(-(t-t_m)^2/8(\Delta t_m)^2) \qquad (6),$$

if the mixing zone is large.

If either $T_1-T_2=\delta$ condition is not met or d does not satisfies equation (4), the selection rules for each pulse will not be satisfied. As a result, the resulting third wave $u_3$ will be diminished or attenuated. It should be noted that there will be additional complexity to the resulting third signal expressed in equation (3) if the earth absorption Q effect is large.

If $T_1-T_2=\delta$ and d satisfies equation (4), the detected signal $u_3(R,t)$ at a receiver R at 16 will be the broadcast signal $u3(M_c, t)$ emanating from the center of the mixing zone $M_c$ which is time delayed by the travel time $T_3$. Signal u3(R,t) at the received can be expressed by equation (7) as follows.

$$u_3(R, t) \propto \sum_n E3_m(t - T_m - T_1 - T_3) * \qquad (7)$$

$$\exp(i*(1-d)*\omega_m*(t-T_m-T_1-T_3)))*\exp(i\zeta_m)$$

If u3(R,t) is cross-correlated with the template signal us(t) expressed by the following equation (8).

$$u_s(t) = \sum_n W_m(t - T_m) * \exp(i * g(\omega_m) * (t - T_m)) * \exp(i\zeta_m), \qquad (8)$$

where $W_m(t)$ is a selected or chosen envelope and $g(\omega_m)$ is a selected or chosen function of frequency as in standard signal processing of chirped signal, the resulting signal will be a frequency band-limited spike that occurs at time $t=T_1+T_3$ provided that the signals $u_1$ and $u_2$ compose a dense set of $\omega_m$ spanning the frequency range $\omega_{min}$ and $\omega_{max}$. The band-limited spike has the frequency range $(1-d)*\omega_{min}$ and $(1-d)*\omega_{max}$ or a frequency content composed of a series of discrete frequencies corresponding to each value of $(1-d)*(\omega 1_m-\omega 2_m)$ for m=1 through M. The function $g(\omega_m)$ in equation (8) can be selected appropriately. The selection of an appropriate function $g(w_m)$ may be based on the shape of the expected modulated signal within the measured signal $u_3$ to achieve the best non-linear signal extraction. $g(\omega_m)$ depends on frequency fraction d. For example, the function $g(\omega_m)$ can be selected such that $g(\omega_m)=(1-d)*\omega_m$. However, other functions can also be selected.

The band-limited spike is effectively a signal originating from a micro-seismic event that occurred at the mixing zone at time $T_1$. The signal from the micro-seismic event at the mixing zone propagates towards the receiver during time $T_3$. The receiver detects the signal at time $T_1+T_3$.

Figure 3A:
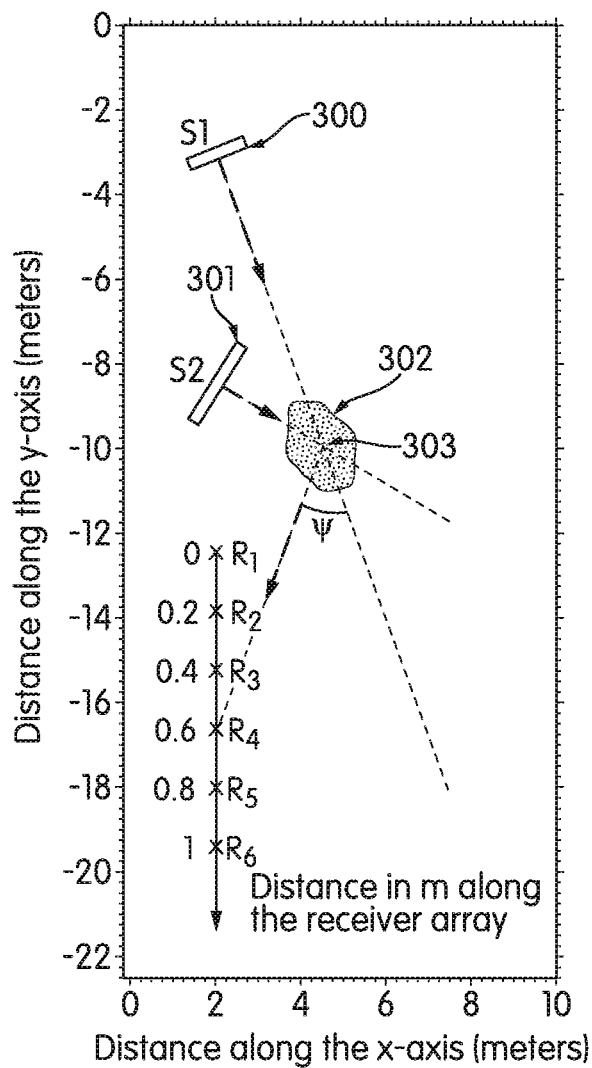
FIG. 3a depicts schematically a position of the first and second acoustic sources and receiver array, according to an embodiment of the present invention.

The correlated measured signal has the following properties. First, the correlated signal contains a sharp band-limited spike, corresponding to the non-linear interaction at the mixing zone, only if the start time difference δ between first and second primary coded signals is equal to the difference between the travel time $T_1$ from the first acoustic source S1 to the mixing zone and the travel time $T_2$ from the second acoustic source S2 to mixing zone MZ (shown in FIG. 3a), i.e. $\delta=T_1-T_2$. If this condition is not met, the correlated signal is highly suppressed. Second, if the condition $\delta=T_1-T_2$ is met, the band-limited spike occurs on the correlated signal at the time T which is equal to a sum of the travel time from the first primary acoustic source to the mixing zone and the travel time from the mixing zone MZ to the receiver Ri within the receiver array 16, as shown in FIG. 1, i.e., $T=T_1+T_3=\delta+T_2+T_3$. Third, increasing the duration of the coded signal train, i.e., increasing the number of pulses M in the broadcast train (in the first signal u1 and the second signal $u_2$), improves discrimination of signal from noise, because the noise does not have the form of the template signal $u_s$.

Figure 3B:
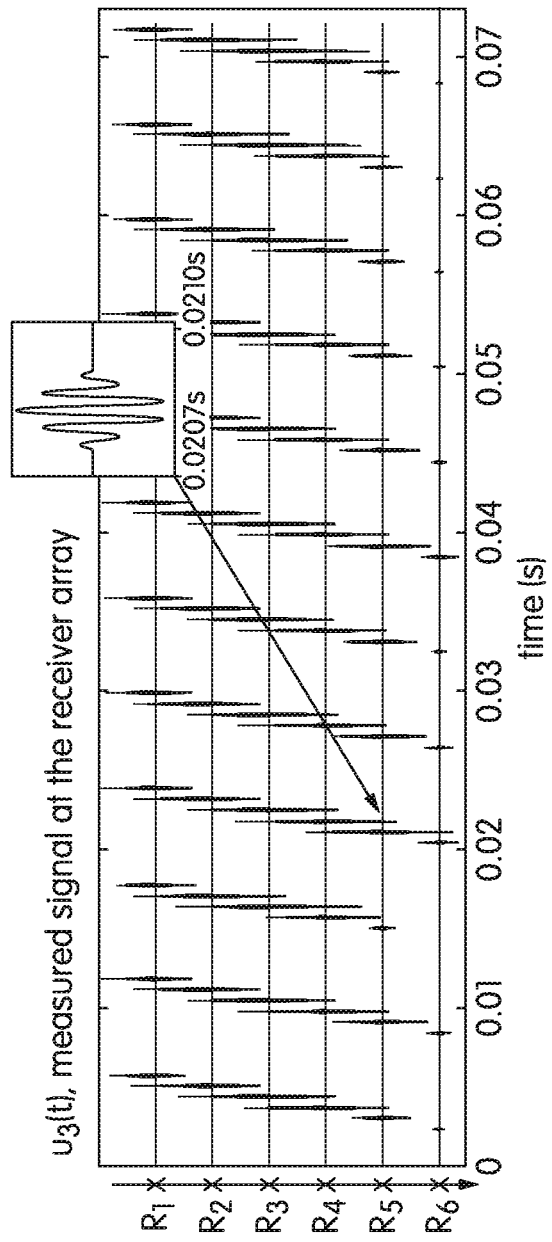
FIG. 3b shows computer simulated signals generated by non-linear interaction, from a broadcast of two pulse sequences, received and recorded at six receivers of a receiver array, according to an embodiment of the present invention.
Figure 3C:
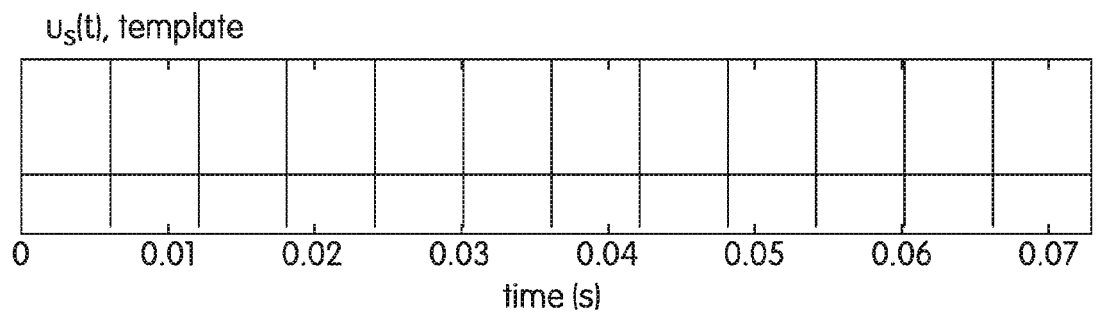
FIG. 3c depicts a template signal used to extract a correlated signal at the receiver array, according to an embodiment of the present invention.
Figure 3D:
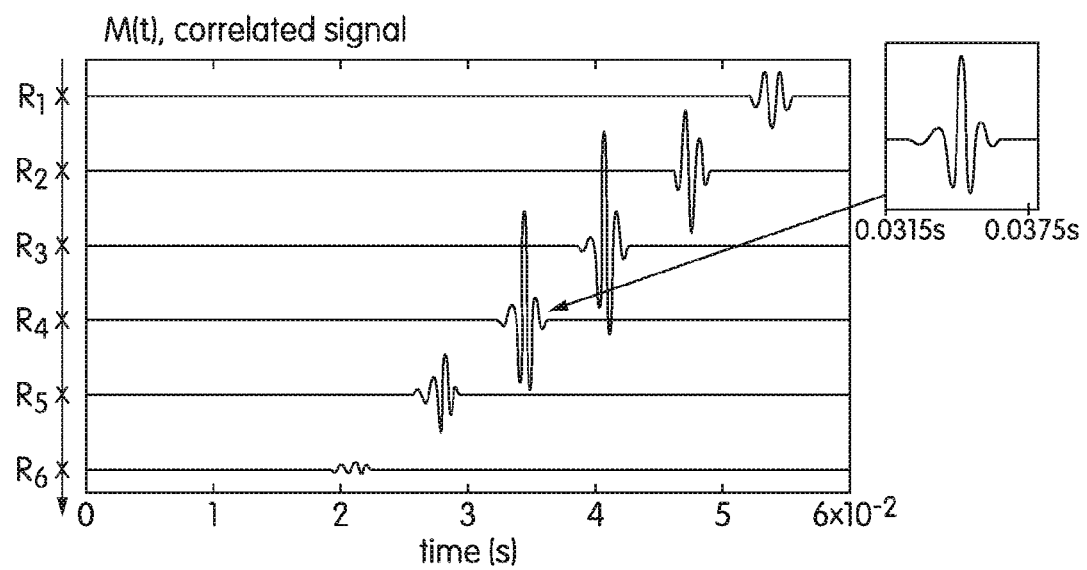
FIG. 3d shows the result of a correlation process between the template signal shown in FIG. 3c with the recorded or measured signal shown in FIG. 3B at each considered receiver, according to an embodiment of the present invention.
Figure 4A:
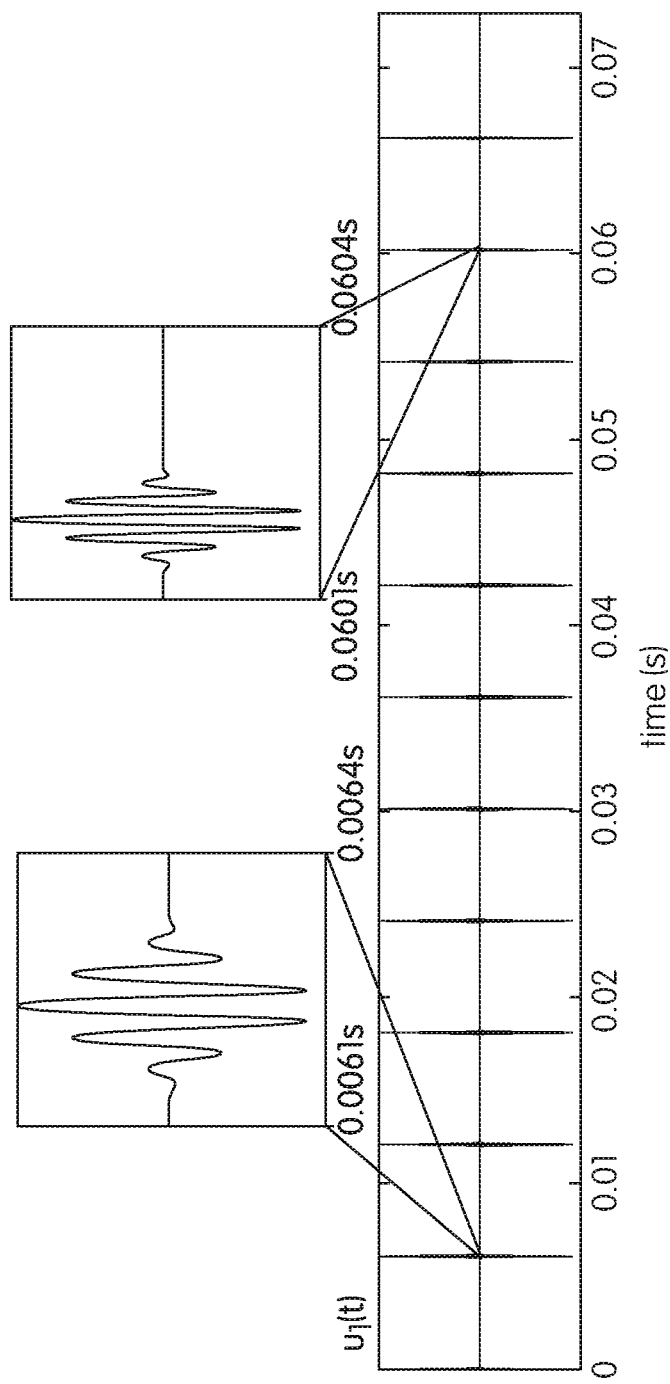
FIGS. 4a and 4b show, respectively, the coded signals from the first acoustic source and the second acoustic source, according to an embodiment of the present invention.
Figure 4B:
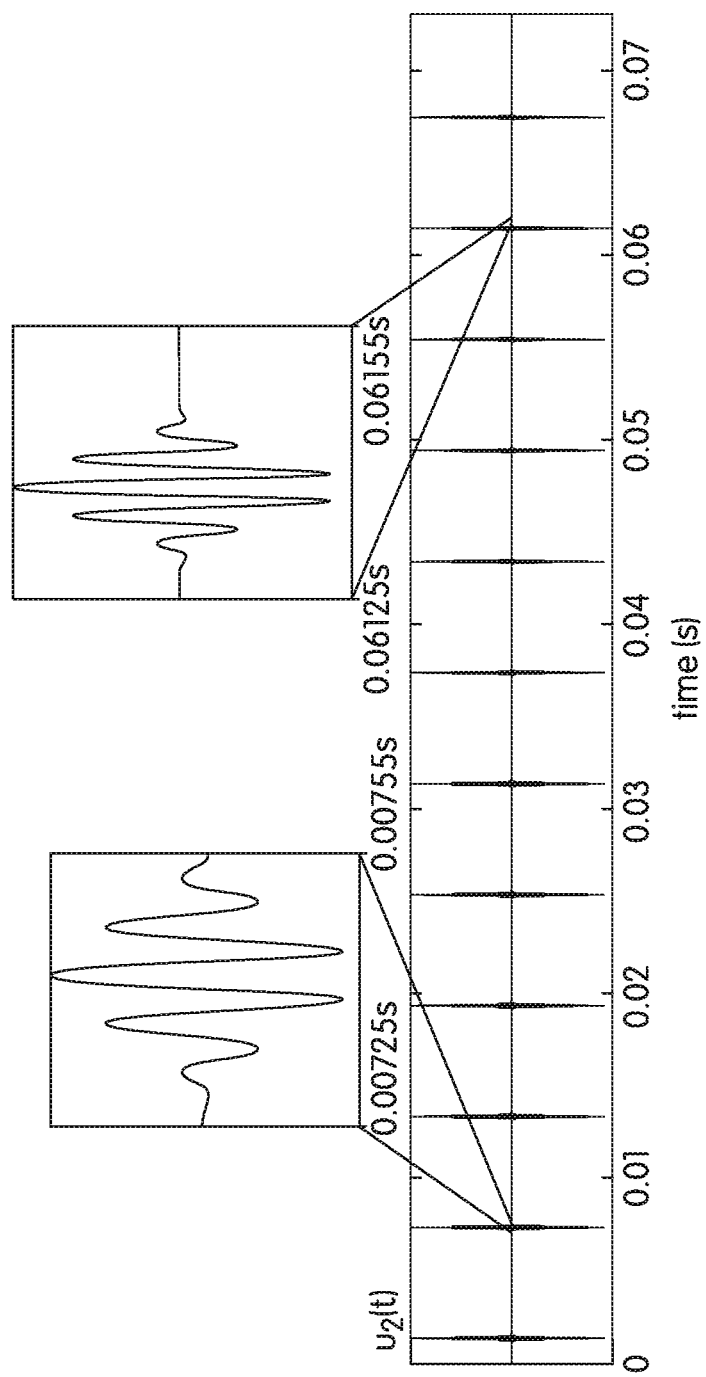

Numerical simulation resulting from a case where the first source S1 and second source S2 emit acoustic beams of coded signal trains $u_1(t)$ and $u_2(t)$ consisting of sequential acoustic pulses with Gaussian envelopes are shown in FIGS. 3b-3d. In this non-limiting example, coded signals of 12 pulses are used with frequency pairs (22,960 Hz, 14,920 Hz) (24,960 Hz, 16,224) (28,000 Hz, 18,200 Hz) (30,280 Hz, 19,680 Hz) (32,080 Hz, 20,852) (34,820 Hz, 22,640 Hz) (37,880 Hz, 24,620) (40,000 Hz, 26,000 Hz) (44,800 Hz, 29,120 Hz) (48,720 Hz, 31,680 Hz) (52960 Hz, 34,440 Hz) (57,600 Hz, 37,440 Hz). The coded pulses $u_1(t)$ and $u_2(t)$ from sources S1 and S2 are shown in FIGS. 4a and 4b, respectively. The frequency ratio $d=\omega_2/\omega_1$ between the pairs is a constant 0.65. The start time difference $\delta$ between the two signal trains $u_1$ and $u_2$ is chosen to be equal to $(T_1-T_2)$. Numerical simulation of the non-linear interaction due to the broadcast of the two coded wave trains $u_1$ and $u_2$ is performed on a computer. The emulated micro-seismic event signals due to non-linear interaction from a broadcast of two sequential pulses received and recorded at six receivers of a receiver array are shown in FIG. 3b. Each receiver $R_i$ is indexed from 1 to 6 and is shown on FIG. 3a with its distance in m along the receiver array. The template $u_s$ for the returning coded signal is shown in FIG. 3c. The result of correlation between the template signal with the recorded signal at each considered receiver is shown in FIG. 3d. The resulting correlated signal at each receiver shown in FIG. 3d shows a very sharp band-limited spike. This sharp band-limited spike occurs at the time $T=T_1+T_3$ where $T_1$ is the travel time from the source S1 to the center of the mixing zone MZ and $T_3$ is the travel time from the center of the mixing zone MZ to each receiver Ri. In one embodiment, $T_3$ is different for each receiver Ri and is the cause of the move-out of the correlation spike along the receiver array as shown on FIG. 3d.

The numerical simulation shown in FIGS. 3b-3d clearly illustrates the power and utility of the coding scheme. It allows for computer processing of the recorded signals at the receivers to generate correlated records that contain band-limited spike signals with strength proportional to the strength of the non-linear interaction at the mixing zone MZ. The arrival time T of the band-limited spike is equal to the total travel time from source S1 to mixing zone MZ and back to receiver Ri. The amplitude of the band-limited spikes vary with the receiver position with a maximum occurring at a particular receiver, the location of which is dependent on the scattering angle $\psi$ of the non-linear interaction at mixing zone MZ. The scattering angle $\psi$ is dependent on the properties of the material or medium, e.g. Vp/Vs velocity ratio, at the mixing zone MZ. It should be noted that this result is a characteristic of the coding scheme. The use of Gaussian envelopes and coded signals in conjunction with templates are non-limiting examples used for the purpose of illustrating the coding scheme and its characteristics. Variants of $u_1, u_2$ and $u_s$ can be considered in order to optimize the performance of the correlation process in term of resolution and signal to noise ratio in response to various considerations imposed by applications.

Figure 5A:
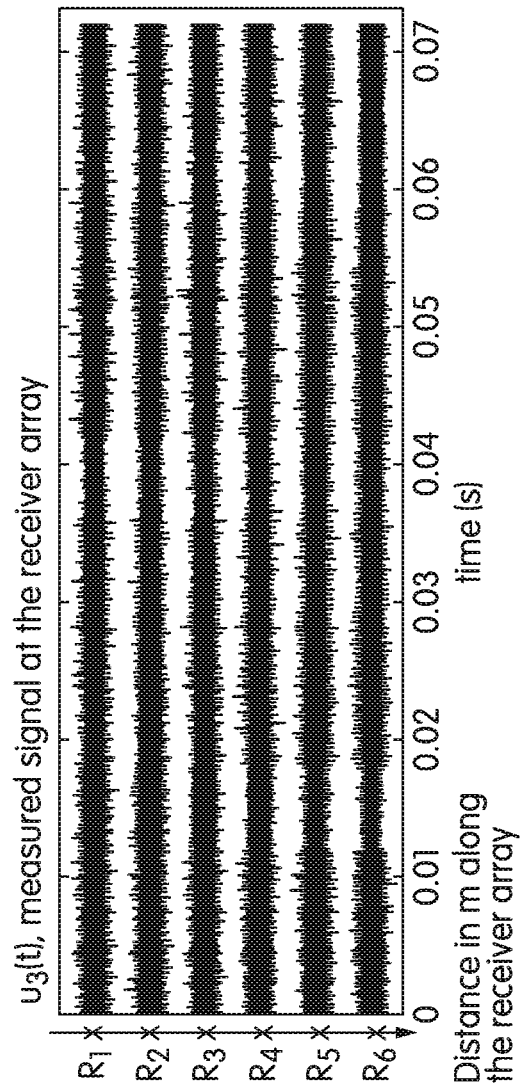
FIG. 5a shows the simulated received signal containing noise recorded at 6 receivers of the receiver array, according to an embodiment of the present invention.
Figure 5B:
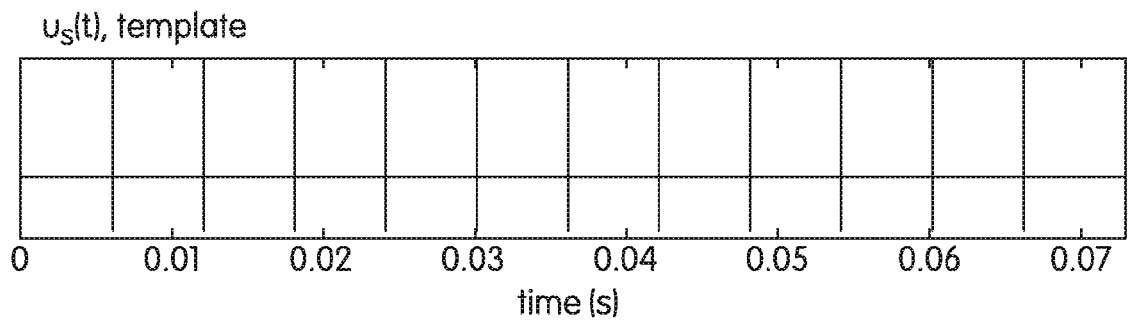
FIG. 5b shows an example of a template signal, according to an embodiment of the present invention.
Figure 5C:
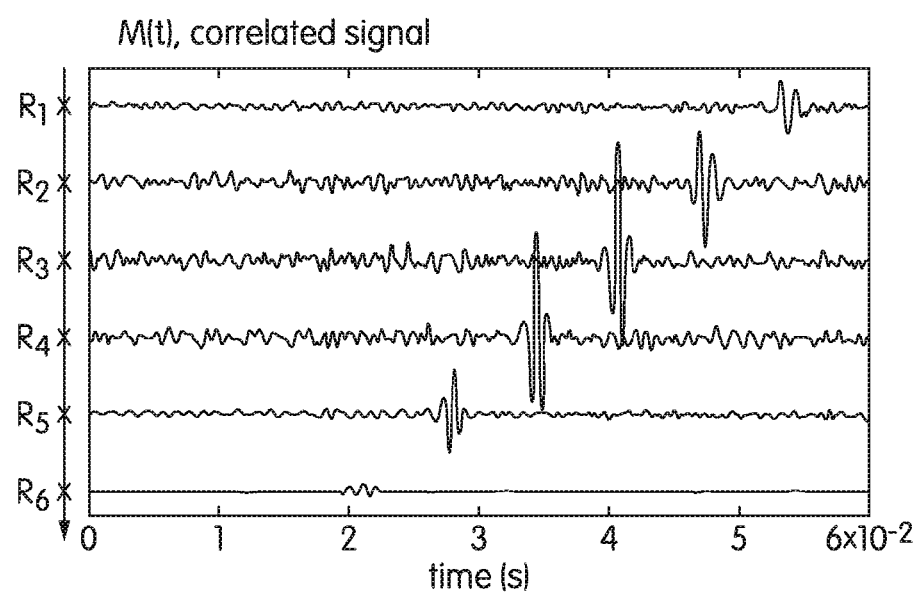
FIG. 5c shows the signal retrieved from the noisy signals on the same receivers when correlating the noisy signals shown in FIG. 5a with the coded template signal shown in FIG. 5b, according to an embodiment of the present invention.

In some aspects of the present disclosure, coded acoustic signals in the primary acoustic signal can also be used to enhance the amplitude and focusing of the non-linear signal propagating towards the receiver, and to improve signal detection sensitivity and signal to noise ratio. FIGS. 5a-5c show an example of an application of the coded signal scheme to a noisy time series signal generated by numerical simulation. The noisy times series signal simulates a signal returning to the borehole as a result of non-linear interaction. White Gaussian noise with an amplitude 10% larger than the amplitude of the non-linear interaction signal is added to the time-series signal produced by the numerical simulation of wave propagation in a non-linear model before the correlation with the coding template is applied. The configuration is similar as that shown in FIG. 3a. FIG. 5a shows the simulated receiving signal containing noise recorded at 6 receivers of the receiver array 16. FIG. 5c shows the signal retrieved from the noisy signals (in this case the simulated noisy signals) on the same receivers when correlating with the coded template $u_s(t)$ of 12 pulses shown in FIG. 5b. The coding scheme is thus shown to effectively extract the signal from the non-linear interaction and minimize the noise, a useful characteristic for field applications.

When S1 and S2 emit acoustic waves instead of acoustic beams, the measurement M(Ri,t) of the coding and subsequent correlation of the measured signal at any receiver Ri in the medium, denoted as M(Ri,t), is the sum of all the acoustic pulses by all points Mc in the medium that satisfy the conditions T1−T2=δ and d satisfying equation (4). Hence, for every time difference and frequency ratio (δ, d) pair, there are a number of Mc points, denoted as Mc(δ, d), that satisfy the conditions T1−T2=δ and d satisfying equation (4). The equation M(Ri,t) for each points i can be expressed by the following equation (9).

$$M(Ri, t) = \sum_{Mc(\delta,d)} A(Mc) * WB[t - T(S1, Mc) - T(Mc, Ri), (1-d)\omega_{min}, (1-d)\omega_{max}] \quad (9)$$

where A(Mc) is an amplitude factor that takes into account propagation effects and non-linear mixing strength at Mc;
where Σ denotes a summation over all mixing zones with the center at Mc(δ, d);
where T(S1, Mc) is the travel time from source S1 to a particular Mc(δ, d);
where T(Mc,Ri) is the travel time from a particular Mc(δ, d) to receiver Ri; and
where WB(t, $\omega_{min}$, $\omega_{max}$) is a band limited spike with frequency range between $\omega_{min}$ and $\omega_{max}$.

Hence as defined by Equation (9), the decoded measurement M(Ri,t) comprises a plurality of measurements of a number of micro-seismic events that occur at the locations Mc(δ, d) in the medium with the receiving time of the micro-seismic events at a receiver Ri corresponding to the total travel time from S1 to the locations Mc(δ, d) and from the locations Mc(δ, d) to the receiver Ri. It should be noted, however, that the strength of the micro-seismic event is proportional to the non-linear properties of the rock at the location of the micro-seismic event locations Mc(δ, d) after correction for the propagation effects and mixing kinematic effects.

As it can be appreciated, the coding scheme shown in FIG. 2 is only one example of a coding scheme allowing for measurements that can be processed into emulated micro-seismic events. There are many variations to this coding scheme. For example, in one embodiment, the period between the pulses for each frequency can be variable with specified time intervals that can be random or periodic. In one embodiment, the amplitude of each pulse can be variable with specified values that can be random or periodic. In one embodiment, the signal time period (i.e., times period between pulses) can be variable. In one embodiment, the modulated signal with the pulse may itself be a composition or a superposition of a sequence of modulated signals arranged at variable listening periods in between the modulated signals so as, for example, to enhance signal to noise ratio of the emulated micro-seismic events. As it can be appreciated, the above embodiments can be implemented separately or combined in any desired fashion to achieve any desired coding scheme.

Figure 6:
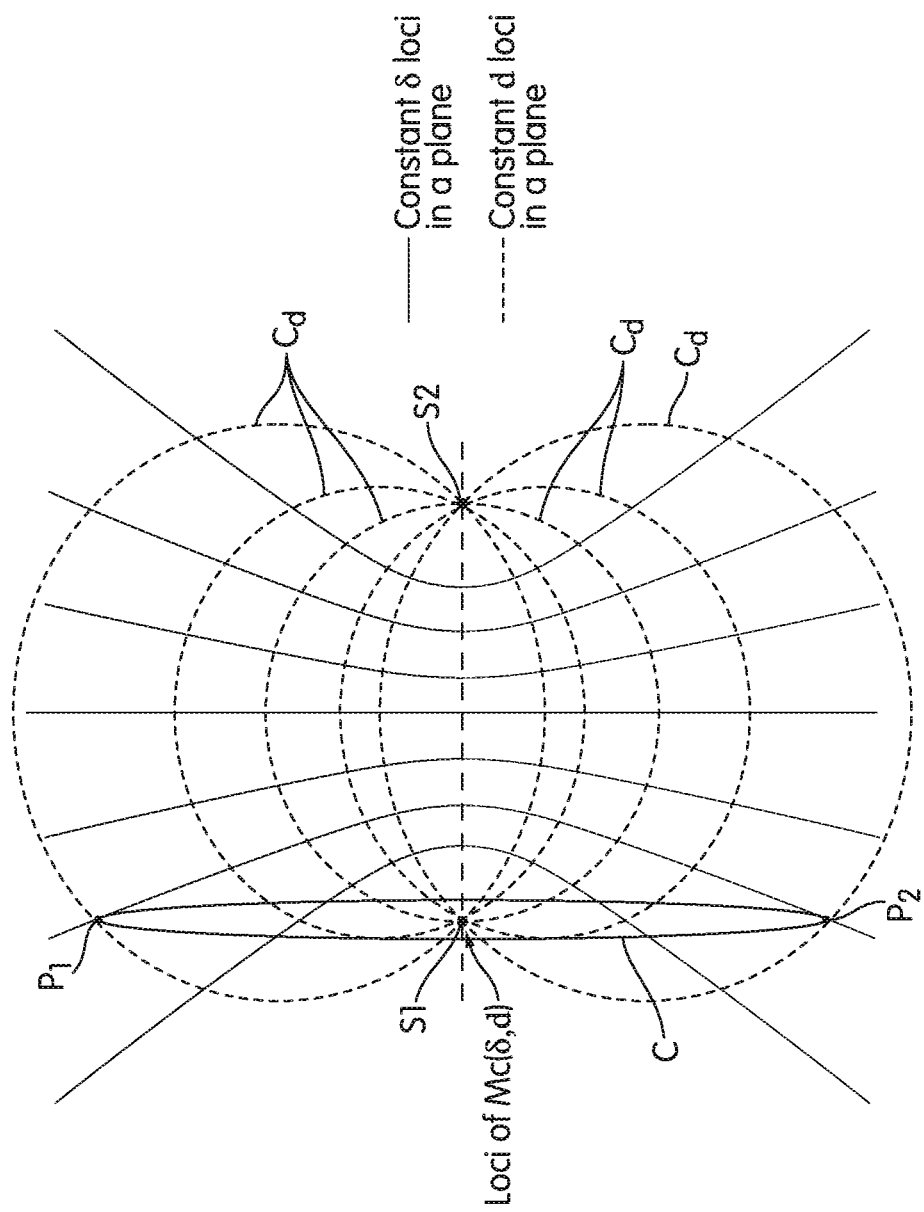
FIG. 6 shows a position of the locations mixing zones Mc(δ, d), for a pair (δ, d) of start time difference δ between the first acoustic signal and the second acoustic signal and frequency ratio d, in a plane containing the first acoustic source and the second acoustic source when the medium has constant acoustic velocities of propagation but variable non-linear earth parameters, according to an embodiment of the present invention.

FIG. 6 shows a position of the locations Mc(δ, d) in a plane containing the first acoustic source S1 and the second acoustic source S2 when the medium has constant acoustic velocities of propagation but variable non-linear earth parameters, according to an embodiment of the present invention. The loci of points of constant δ are vertically oriented hyperbolas in a plane containing the sources S1 and S2. The loci of the points at constant frequency ratio d define a plurality of circles $C_d$. The center of the circles $C_d$ is on the bisector line of the S1 to S2 segment. The circles pass through the points S1 and S2 in the same plane. Therefore, for each (δ, d) pair, there are exactly two points (e.g., $P_1$ and $P_2$) in a plane for Mc(δ, d). By rotating the plane around the S1S2 axis, the loci of Mc(δ, d) can be defined as a circle C(δ, d), having a center on the S1S2 axis for each (δ, d) pair. If all values of (δ, d) pairs are scanned, micro-seismic events for all locations in the volume space in the medium surrounding the S1S2 line can be created.

It can be seen that when the assumption of constant acoustic velocity is relaxed, the loci of Mc(δ, d) would be more complex due to propagation effects, e.g. ray bending and wave front complexity. However, regardless of complexity within the non-linear medium (e.g., different wave front velocities, etc.), micro-seismic events can be emulated to occur at the intersection of the wavefronts from the two sources S1 and S2 with the measurement and coding scheme described above.

Figure 7:
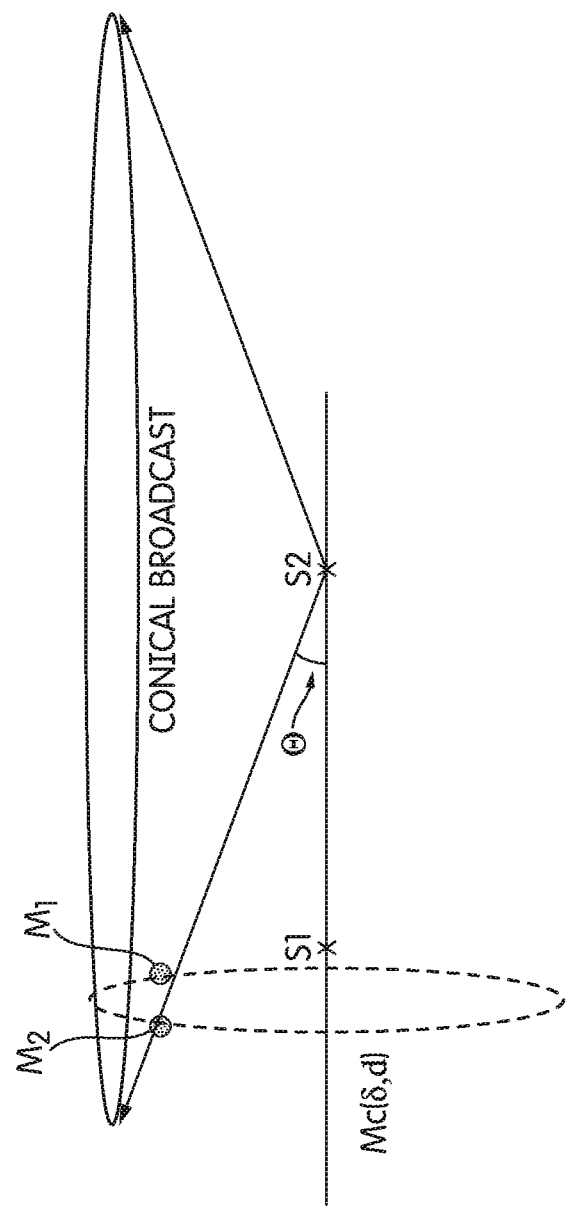
FIG. 7 depicts a situation where the first acoustic source is a source for generating an acoustic wave and the second acoustic source generates a conical acoustic broadcast, according to an embodiment of the present invention.

In one embodiment, the emulated micro-seismic events can be localized even further if S1 and S2 acoustic sources have a beam radiation pattern. FIG. 7 depicts a situation where acoustic source S1 is an array source for generating a beam of radiation, according to an embodiment of the present invention. In one embodiment, the array source S1 is positioned perpendicular to S1S2 axis. By suitable start time difference of source elements, an array source S1 can generate acoustic waves at a specific inclination to the S1S2 axis. The acoustic wavefront of source S1 is restricted to a cone, for example. As shown in FIG. 7, the axis of the cone is perpendicular to the S1S2 axis. Therefore, emulated micro-seismic events are restricted to two points $M_1$ and $M_2$ in the medium at the intersection of the cone and loci circle C(δ, d) as shown in FIG. 7. Thus, the radiation beam patterns of S1 and S2 control where the emulated micro-seismic events can occur in the medium.

In earthquake seismology, by assuming a model of the acoustic propagation velocities of the medium, a time reversal operation can be performed on seismic measurements. The time reversal modeling operation can refocus the acoustic wave back to a peak at the time of origination of the seismic event. The strength of the focused energy peak at the time of origination is a function of the strength of the initial seismic event. The general concept of time reversal has generated many applications in the field of acoustics. The general time reversal methodology commonly known as reverse time migration or RTM has been applied to imaging in a complex medium such as in the exploration of oil and gas (see, George A. McMechan, Determination of source parameters by wavefield extrapolation, Geophysical Journal of the Royal Astronomical Society, Volume 71, Issue 3, pages 613-628, December 1982), the entire contents of which is incorporated herein by reference.

The time reversal methodology can be applied to the emulated micro-seismic measurements described in the above paragraphs. In the present application, the time reversal operations can focus the waves back to the time and place of origination (i.e., to positions Mc(δ, d) and time T(S1, Mc) as noted in the above paragraphs) of the micro-seismic events. As stated in the above paragraphs, the strengths of the micro-seismic events at the time of origination are proportional to the non-linear properties at the location of the micro-seismic events. Therefore, the time reversal operation can be used as a tool for the determination of relative values of the non-linear properties at the points of origination Mc(δ, d). Hence, if the time reversal operation is performed on the emulated micro-seismic events for all pairs of (δ, d), the non-linear properties at all locations Mc(δ, d) can be quantified. By combining the values of non-linear properties of all locations Mc(δ, d), three dimensional (3D) images of relative strength of the non-linear properties of the medium around the source S1 and S2 can be constructed.

Conventional standard imaging methods in exploration seismology such as Kirchhoff, Beam and Wave Equation Migration can also be modified and applied to the present non-linear acoustic interaction to develop 3D images of the relative strength of the non-linear properties of the medium from the measurements of the emulated micro-seismic events assuming a propagation velocity model of the medium. Other advanced inversion methods known to various industries can be applied to the emulated micro-seismic events.

In an embodiment of the use of the Kirchhoff imaging methodology for the emulated micro-seismic events resulting from a non-linear interaction of two acoustic waves in a non-linear medium is described in detail in the following paragraphs.

In one embodiment, the emulated micro-seismic events can be expressed as M(Ri, t). For every given point Mc in a medium, the travel time T(Ri,Mc) from the interaction zone Mc to the receiver Ri of the receiver array 16 (e.g., R1, R2, etc.) and the travel time T(S1, Mc) from acoustic source S1 to receiver (e.g., R1, R2, etc.) can be computed using the propagation velocity model. In one embodiment, the amplitude of the wave propagation A(S1, Mc) from source S1 to interaction zone Mc, the amplitude of the wave propagation A(S2, Mc) from source S2 to interaction zone Mc and the amplitude of the beam propagation A(Mc, Ri) from interaction zone Mc to receiver Ri (e.g., R1, R2, etc.) can also be computed. The image value of the non-linear properties can be expressed by the following equation (10).

$$I(Mc) = \sum_{Ri} M(Ri, t = T(Ri, Mc) + T(Ri, S1)) * \frac{1}{A(S1, Mc)} * \frac{1}{A(S2, Mc)} * \frac{1}{A(Mc, Ri)} \quad (10)$$

In one embodiment, appropriate small "noise factors" may be introduced into equation (9) in calculating inverse factors, e.g. (1/A(S1, Mc)), to stabilize these inverse weighting factors in accordance with standard signal processing best practice. If there is a micro-seismic event at Mc, the summation of all the measurement responses Ri coming from the micro-seismic event at Mc will be in phase while the contribution of all other micro-seismic events at other locations will be out of phase. Therefore, I(Mc) computed from Equation (9) contains only information from the micro-seismic event at Mc.

Equation (10) shows how a 3D image can be constructed from emulated micro-seismic events generated by acoustic waves from a pair of acoustic sources S1 and S2. Multiple images I(Mc;S1,S2) can be constructed from many pairs of acoustic sources S1 and S2 at different locations. If the propagation velocity model is correct, these images will have to be the same. If they are not the same, there are errors in the propagation velocity model. This self-consistent condition can be used to determine the correct propagation velocity model as well as the local velocity ratio Vp/Vs at the mixing location Mc.

The multiple images I(Mc;S1,S2) for a plurality of locations of S1 and S2 can be constructed assuming an initial propagation velocity model and local velocity ratio Vp/Vs ratio at the mixing location Mc. Updates to propagation velocity model by velocity tomography method can be performed to minimize the differences in the obtained (3D) images I(Mc;S1, S2). In one embodiment, the updating process can be iterated until the differences in the obtained images I(Mc;S1,S2) are minimized. The multiple images I(Mc;S1,S2) can then be combined to create a final image of non-linear properties of the medium or the local velocity ratio Vp/Vs or both.

In some aspect of the present disclosure, the above described data acquisition, processing and imaging can be used to perform time-lapse surveys. Variations in non-linearity or the velocity ratio Vp/Vs caused by, for example, stress, formation fluid pressure or saturation changes can be visible in d, δ, t space and thus may be localized approximately with no need for complex processing to transform into mapped properties.

The methods and systems described herein can be applied to any medium that sustain acoustic wave propagation. For example, the methods and systems can be applied to seismology, borehole logging, medical ultra-sound imaging, non-destructive testing and material sciences such as, but not limited to, locating damage in diffusion bonded samples, locating damage in explosives, locating damage in bone, correlating crack density and nonlinearity in composites, locating nonlinear features inside the bulk of a solid, etc. The methods and systems can also be used for general nonlinear non-destructive evaluation (NDE) of a material.

In addition, it must be appreciated that the term processor is used herein to encompass one or more processors. The one or more processors can be configured to implement the methods or portions of the methods described herein. The one or more processors can be located in one or more computers such as, for example, in a distributed computing environment comprising a plurality of computers. In some embodiments, programs for performing methods in accordance with embodiments of the invention can be embodied as program products in a computer such as a personal computer or server or in a distributed computing environment comprising a plurality of computers. Where reference is made to a processor that term should be understood to encompass any of these computing arrangements. The computer may include, for example, a desktop computer, a laptop computer, a handheld computing device. The computer program products may include a computer readable medium or storage medium or media having instructions stored thereon used to program a computer to perform the methods described above. Examples of suitable storage medium or media include any type of disk including floppy disks, optical disks, DVDs, CD ROMs, magnetic optical disks, RAMs, EPROMs, EEPROMs, magnetic or optical cards, hard disk, flash card (e.g., a USB flash card), PCMCIA memory card, smart card, or other media. Alternatively, a portion or the whole computer program product can be downloaded from a remote computer or server via a network such as the internet, an ATM network, a wide area network (WAN) or a local area network.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. As a further example, it is to be understood that the present invention contemplates that, to the extent possible, one or more features of any embodiment can be combined with one or more features of any other embodiment.

What is claimed is:

1. A method of generating a micro-seismic event in a medium from a non-linear interaction to characterize the medium, the method comprising:

generating, by a first acoustic source, a first coded acoustic signal comprising a first plurality of pulses arranged as a time sequence, the first plurality of pulses being separated in time, each pulse comprising a modulated signal at a central frequency, wherein central frequencies of two consecutive pulses are different;

generating, by a second acoustic source, a second coded acoustic signal comprising a second plurality of pulses arranged as a time sequence, the second plurality of pulses being separated in time, wherein a separation in time between centers of two consecutive pulses is the same as a separation in time between centers of two corresponding pulses in the first plurality of pulses, wherein a start time difference is provided between a start time of a broadcast of the second plurality of pulses and a start time of a broadcast of the first plurality of pulses, wherein each pulse comprises a modulated signal and a central frequency of the modulated signal within each pulse in the second plurality of pulses is a selected fraction d of the central frequency of the modulated signal for the corresponding pulse in the first plurality of pulses;

wherein the first acoustic source and the second acoustic source are controllable such that trajectories of the first and the second acoustic signals intersect in a mixing zone within the medium;

receiving, by a receiver, a detected signal including a third signal being generated by a non-linear mixing process from the first acoustic signal and the second acoustic signal in the mixing zone;

performing, by a processor, data processing on the detected signal, or correlating with a coded signal template, or both, to extract the third signal generated by the non-linear mixing process over noise or over signals generated by a linear interaction process, or both, to obtain an emulated micro-seismic event signal occurring at the mixing zone of the first and second acoustic signals; and characterizing properties of the medium or creating a 3D image of the properties of the medium, or both, based on the emulated micro-seismic event signal.

2. The method according to claim 1, wherein generating the first coded acoustic signal comprises generating the first acoustic signal such that a separation in time between the centers of two consecutive pulses in the first plurality of pulses is greater than a time duration of each pulse.

3. The method according to claim 1, wherein the third signal generated by the non-linear mixing process and received at the receiver comprises a third plurality of pulses arriving in a time sequence and separated in time, wherein a separation in time between centers of two consecutive pulses is the same as the separation in time between centers of two consecutive pulses in the first plurality of pulses, wherein each pulse in the third plurality of pulses comprises a modulated signal having a central frequency of each pulse that is equal to a difference between the central frequency of the corresponding pulse of the first plurality of pulses and the central frequency of the corresponding pulse of the second plurality of pulses, wherein an arrival time at the receiver of each pulse of the third plurality of pulses is time delayed relative to a generation of a corresponding pulse of the first plurality of pulses by a total of a travel time from the first acoustic source to a center of the mixing zone and a travel time from the center of the mixing zone to the receiver.

4. The method according to claim 1, further comprising repeating the generating of the first signal, the generating of the second signal, the receiving of the third signal and the performing of data processing or correlating with a coded signal template, or both, for a range of start time differences and a range of frequency fractions d to obtain signals from emulated micro-seismic events generated at a plurality of mixing zones.

5. The method according to claim 1, wherein generating the first signal comprises generating a first signal that is a sum of a plurality of pulses, wherein each pulse has a signal amplitude equal to the product of an envelope function and a modulated signal function, and wherein generating the second signal comprises generating a second signal that is a sum of a plurality of pulses, wherein each pulse has a signal amplitude equal to the product of an envelope function and a modulated signal function.

6. The method according to claim 1, wherein generating the first signal and the second signal comprises generating a first signal $u_1(t)$ and a second signal $u_2(t)$ in the form:

$$u_1(t) = \sum_m E1_m(t-t_m) * \exp(i\omega_m * (t-t_m)) * \exp(i\zeta_m)$$

and $$u_2(t-\delta) = \sum_m E2_m(t-(t_m+\delta)) * \exp(id * \omega_m * (t-(t_m+\delta))) * \exp(i\zeta_m)$$

where m is an index number associated with a pulse;

$\Sigma$ denotes a summation over index m=1 to M with M being an integer equal to or greater than 1;

$E1_m(t-t_m)$ is an amplitude envelope of pulse m of the first acoustic signal $u_1$;

$E2_m(t-t_m-\delta)$ is an amplitude envelope of pulse m of the second acoustic signal $u_2$;

$\omega_m$ is the central frequency of the modulated signal of pulse m of the first acoustic signal $u_1$;

$(d*\omega_m)$ is the central frequency of the modulated signal of pulse m of the second acoustic signal $u_2$;

d is a frequency ratio between the frequency $\omega_m$ in the first plurality of pulses and the frequency $d*\omega_m$ in the second plurality of pulses, where d is a real positive number;

$\delta$ is the start time difference between the generation of the first acoustic signal $u_1$ and the second acoustic signal $u_2$;

$\exp(i\omega_m*(t-t_m))$ is the modulated signal within the pulse m of the first acoustic signal $u_1$;

$\exp(id*\omega_m*(t-t_m-\delta))$ is the modulated signal within the pulse m of second acoustic signal $u_2$;

$t_m$ is the time pulse m is generated in the first acoustic signal $u_1$;

$t_m+\delta$ is the time pulse m is generated in the second acoustic signal $u_2$; and $\exp(i\zeta m)$ is a phase term of each pulse m within the first signal $u_1$ or second signal $u_2$.

7. The method according to claim 1, wherein the third signal $u_3(t)$ being generated by a non-linear mixing process is in the form:

$$u_3(R,t) \propto \sum_n E3_m(t-t_m-T_1-T_3)) *$$
$$\exp(i*(1-d)*\omega_m*(t-t_m-T_1-T_3))) * \exp(i\zeta_m)$$

where:

$E3_m(t-t_m-T_1-T_3)$ is an envelope of a pulse in a third plurality of pulses of the signal u3 generated by non-linear mixing of the first signal and the second signal, $\exp(i*(1-d)*\omega_m*(t-t_m-T_1-T_3))$ corresponds to a third modulated signal within the mth pulse in the third plurality of pulses, $(1-d)*\omega_m$ is a frequency of the modulated signal within the mth pulse in the third plurality of pulses which is a difference between the central frequency $\omega_m$ of the first modulated signal within the mth pulse of the first plurality of pulses and the central frequency $d*\omega_m$ of the second modulated signal within the mth pulse of the second plurality of pulses, d is a selected frequency ratio, t is the signal time, R is label of receiver or location of receiver $(T_1+T_3)$ is a time when the mth pulse in the third plurality of pulses arrives at the receiver, and $\zeta_m$ is a phase of each pulse m and $\exp(i\zeta_m)$ is a phase term of each pulse m.

8. The method according to claim 1, further comprising extracting, by the processor, a signal generated by the non-linear mixing process to obtain the signal from the emulated micro-seismic event at the mixing zone of the first and second acoustic signals by correlating the detected signal with a template signal, wherein the template signal comprises a plurality of pulses, wherein the time separation between the center of the plurality of pulses in the template signal are the same as the time separation of the center of the plurality of pulses of the first acoustic signal and wherein the central frequency of the plurality of pulses in the third signal is a function of the central frequency of the plurality of pulses in first acoustic signal and the frequency fraction d.

9. The method according to claim 8, further comprising increasing a number of the first plurality of pulses and increasing a number of the second plurality of pulses to enhance discrimination of the third signal generated by the non-linear mixing process over noise or over signals generated by a linear interaction process, or both.

10. The method according to claim 1, further comprising extracting, by the processor, the third signal generated by the non-linear mixing process to obtain the signal from the emulated micro-seismic event at the mixing zone of the first and second acoustic signals by correlating the detected signal with a template signal, wherein the template signal $u_s$ is in the form:

$$u_s(t) = \sum_n W_m(t-t_m) * \exp(i*g(\omega_m)*(t-t_m)) * \exp(i\zeta_m)$$

Where:

$W_m(t-t_m)$ is an amplitude envelope of an mth pulse in the template signal, exp $(i^* g(\omega_m)^*(t-t_m))$ corresponds to modulated signal within the mth pulse in the plurality of pulses of the template signal, $g(\omega_m)$ is a selected function of the modulated signal depending on frequency fraction d, within the mth pulse in the plurality of pulses of the template, t is a propagation time, $t_m$ is a time when the mth pulse in the plurality of pulses is simulated to arrive at the receiver, and $\zeta_m$ is a phase of each pulse n and $\exp(i\zeta_m)$ is a phase term of each pulse m.

11. The method according to claim 10, further comprising:

extracting, by the processor, the third signal from the emulated micro-seismic event at the mixing zone of the first and second acoustic signals by correlating the detected signal at a receiver Ri with a coded template signal $u_s(t)$, and repeating for a plurality of start time differences δ between the second plurality of pulses and the first plurality of pulses and for a plurality of frequency ratios d between the central frequency of the modulated signal within each pulse in the second plurality of pulses and the central frequency of the modulated signal with each corresponding pulse in the first plurality of pulses, the correlating between the template signal and the detected signal to yield, for each start time difference δ and for each frequency ratio d, a correlated signal for each receiver Ri denoted as M(Ri, t), which contains emulated micro-seismic events generated by non-linear interaction at specific mixing locations according to selection rules of non-linear interaction.

12. The method according to claim 11, further comprising calculating, for each start time difference δ and for each frequency ratio d and the corresponding correlated signal M(Ri, t), the spatial coordinates of emulated micro-seismic events where the two acoustic signals interact non-linearly using locus analysis and travel time calculations based on a velocity model for compression or shear wave velocity.

13. The method according to claim 11, further comprising applying time reversal operations to propagate backward in time the signals of the emulated micro-seismic events to the time and location of origination of the micro-seismic events with a propagation velocity model.

14. The method according to claim 13, further comprising determining relative strengths of the micro-seismic events at the locations of origination, wherein the relative strengths at the locations of origination are proportional to non-linear properties of the medium at the locations of origination of the micro-seismic events.

15. The method according to claim 11, further comprising generating a three-dimensional image of the micro-seismic events or the non-linear properties of the medium, or both, by using Kirchhoff imaging, beam imaging, wave equation imaging, or time reversal method from the correlated signals containing emulated micro-seismic events at the mixing zones of the first and second acoustic signals, wherein the correlated signals are obtained from signals received at a plurality of receivers, wherein the first source and the second source are located at different locations.

16. The method according to claim 11, further comprising repeating the generating of the first signal by the first source a plurality of time by disposing the first source at a plurality of locations and repeating the generating of the second signal by the second source a plurality of time by disposing the second source at a plurality of locations; and repeating the receiving of the third signal a plurality of time by disposing the receiver at a plurality of locations; and generating multiple three dimensional images of the non-linear properties of the medium by using Kirchhoff imaging, beam imaging, wave equation imaging, or time reversal method from the correlated signals containing emulated micro-seismic events at the mixing zones of the first and second acoustic signals, wherein the correlated signals are obtained from signals received at a plurality of receivers.

17. The method according to claim 16, further comprising updating the propagation velocity model by velocity tomography method to minimize the differences in the multiple three dimensional images from received signals from a plurality of locations of the first acoustic source and the second acoustic source.

18. The method according to claim 17, further comprising updating the propagation velocity model and imaging iteratively until the differences between the obtained multiple images are minimized and combining the multiple images to create a final three dimensional image of non-linear properties of the medium or the local velocity ratio Vp/Vs or both.

19. A system for generating a micro-seismic event in a medium from a non-linear interaction to characterize the medium, the system comprising:

a first acoustic source configured to generate a first coded acoustic signal comprising a first plurality of pulses arranged as a time sequence, the first plurality of pulses being separated in time, each pulse comprising a modulated signal at a central frequency, wherein central frequencies of two consecutive pulses are different;

a second acoustic source configured to generate a second coded acoustic signal comprising a second plurality of pulses arranged as a time sequence, the second plurality of pulses being separated in time, wherein a separation in time between centers of two consecutive pulses is the same as a separation in time between centers of two corresponding pulses in the first plurality of pulses, wherein a start time difference is provided between a start time of a broadcast of the second plurality of pulses and a start time of a broadcast of the first plurality of pulses, wherein each pulse comprises a modulated signal and a central frequency of the modulated signal within each pulse in the second plurality of pulses is a selected fraction d of the central frequency of the modulated signal for the corresponding pulse in the first plurality of pulses;

wherein the first acoustic source and the second acoustic source are controllable such that trajectories of the first and the second acoustic signals intersect in a mixing zone within the medium;

a receiver configured to receive a detected signal including a third signal being generated by a non-linear mixing process from the first acoustic signal and the second acoustic signal in the mixing zone; and a processor configured to perform data processing on the detected signal, or correlate with a coded signal template, or both, to extract the third signal generated by the non-linear mixing process over noise or over signals generated by a linear interaction process, or both, to obtain an emulated micro-seismic event signal occurring at the mixing zone of the first and second acoustic signals so as to characterize properties of the medium or create a 3D image of the properties of the medium, or both, based on the emulated micro-seismic event signal.

20. The system according to claim 19, wherein the first acoustic source is configured to generate the first coded acoustic signal such that a separation in time between the centers of two consecutive pulses in the first plurality of pulses is greater than a time duration of each pulse.

21. The system according to claim 19, wherein the third signal generated by the non-linear mixing process and received at the receiver comprises a third plurality of pulses arriving in a time sequence and separated in time, wherein a separation in time between centers of two consecutive pulses is the same as the separation in time between centers of two consecutive pulses in the first plurality of pulses,
wherein each pulse in the third plurality of pulses comprises a modulated signal having a central frequency of each pulse that is equal to a difference between the central frequency of the corresponding pulse of the first plurality of pulses and the central frequency of the corresponding pulse of the second plurality of pulses,
wherein an arrival time at the receiver of each pulse of the third plurality of pulses is time delayed relative to a generation of a corresponding pulse of the first plurality of pulses by a total of a travel time from the first acoustic source to a center of the mixing zone and a travel time from the center of the mixing zone to the receiver.

22. The system according to claim 19, wherein the processor is configured to control the first source and the second source to repeat the generating of the first signal, the generating of the second signal, to control the receiver to repeat the receiving of the third signal and repeat the performing of data processing or correlating with a coded signal template, or both, for a range of start time differences and a range of frequency fractions d to obtain signals from emulated microseismic events generated at a plurality of mixing zones.

23. The system according to claim 19, wherein the first acoustic source is configured to generate a first signal that is a sum of a plurality of pulses, wherein each pulse has a signal amplitude equal to the product of an envelope function and a modulated signal function, and wherein the second acoustic source is configured to generate a second signal that is a sum of a plurality of pulses, wherein each pulse has a signal amplitude equal to the product of an envelope function and a modulated signal function.

24. The system according to claim 19, wherein the first signal comprises a first signal $u_1(t)$ and the second signal comprises a second signal $u_2(t)$ in the form:

$$u_1(t) = \sum_m E1_m(t-t_m) * \exp(i\omega_m * (t-t_m)) * \exp(i\zeta_m)$$

and $$u_2(t-\delta) = \sum_m E2_m(t-(t_m+\delta)) * \exp(id * \omega_m * (t-(t_m+\delta))) * \exp(i\zeta_m)$$

where m is an index number associated with a pulse;
$\Sigma$ denotes a summation over index m=1 to M with M being an integer equal to or greater than 1;
$E1_m(t-t_m)$ is an amplitude envelope of pulse m of the first acoustic signal $u_1$;
$E2_m(t-t_m\delta)$ is an amplitude envelope of pulse m of the second acoustic signal $u_2$;
$\omega_m$ is the central frequency of the modulated signal of pulse m of the first acoustic signal $u_1$;
$(d*\omega_m)$ is the central frequency of the modulated signal of pulse m of the second acoustic signal $u_2$;
d is a frequency ratio between the frequency $\omega_m$ in the first plurality of pulses and the frequency $d*\omega_m$ in the second plurality of pulses, where d is a real positive number;

$\delta$ is the start time difference between the generation of the first acoustic signal $u_1$ and the second acoustic signal $u_2$;
$\exp(i\omega_m*(t-t_m))$ is the modulated signal within the pulse m of the first acoustic signal $u_1$;
$\exp(id*\omega_m*(t-t_m-\delta))$ is the modulated signal within the pulse m of second acoustic signal $u_2$;
$t_m$ is the time pulse m is generated in the first acoustic signal $u_1$;
$t_m+\delta$ is the time pulse m is generated in the second acoustic signal $u_2$; and
$\exp(i\zeta m)$ is a phase term of each pulse m within the first signal $u_1$ or second signal $u_2$.

25. The system according to claim 19, wherein the third signal $u_3(t)$ being generated by a non-linear mixing process is in the form:

$$u_3(R, t) \propto \sum_n E3_m(t-t_m-T_1-T_3)) * \exp(i*(1-d)*\omega_m*(t-t_m-T_1-T_3))) * \exp(i\zeta_m)$$

where:
$E3_m(t-t_m-T_1-T_3)$ is an envelope of a pulse in a third plurality of pulses of the signal u3 generated by non-linear mixing of the first signal and the second signal,
$\exp(i*(1-d)*\omega_m*(t-t_m-T_1-T_3))$ corresponds to a third modulated signal within the mth pulse in the third plurality of pulses,
$(1-d)*\omega_m$ is a frequency of the modulated signal within the mth pulse in the third plurality of pulses which is a difference between the central frequency $\omega_m$ of the first modulated signal within the mth pulse of the first plurality of pulses and the central frequency $d*\omega_m$ of the second modulated signal within the mth pulse of the second plurality of pulses,
d is a selected frequency ratio,
t is the signal time,
R is label of receiver or location of receiver
$(T_1+T_3)$ is a time when the mth pulse in the third plurality of pulses arrives at the receiver, and
$\zeta_m$ is a phase of each pulse m and $\exp(i\zeta_m)$ is a phase term of each pulse m.

26. The system according to claim 19, wherein the processor is configured to extract a signal generated by the non-linear mixing process to obtain the signal from the emulated micro-seismic event at the mixing zone of the first and second acoustic signals by correlating the detected signal with a template signal, wherein the template signal comprises a plurality of pulses, wherein the time separation between the center of the plurality of pulses in the template signal are the same as the time separation of the center of the plurality of pulses of the first acoustic signal and wherein the central frequency of the plurality of pulses in the third signal is a function of the central frequency of the plurality of pulses in first acoustic signal and the frequency fraction d.

27. The system according to claim 19, wherein the processor is configured to extract the third signal generated by the non-linear mixing process to obtain the signal from the emulated micro-seismic event at the mixing zone of the first and second acoustic signals by correlating the detected signal with a template signal, wherein the template signal $u_s$ is in the form:

$$u_s(t) = \sum_n W_m(t - t_m) * \exp(i * g(\omega_m) * (t - t_m)) * \exp(i\zeta_m)$$

Where:

$W_m(t-t_m)$ is an amplitude envelope of an mth pulse in the template signal, exp $(i*g(\omega_m)*(t-t_m))$ corresponds to modulated signal within the mth pulse in the plurality of pulses of the template signal, $g(\omega_m)$ is a selected function of the modulated signal depending on frequency fraction d, within the mth pulse in the plurality of pulses of the template, t is a propagation time, $t_m$ is a time when the mth pulse in the plurality of pulses is simulated to arrive at the receiver, and $\zeta_m$ is a phase of each pulse n and $\exp(i\zeta_m)$ is a phase term of each pulse m.

28. The system according to claim 27, further comprising:
Wherein the processor is configured to extract the third signal from the emulated micro-seismic event at the mixing zone of the first and second acoustic signals by correlating the detected signal at a receiver Ri with a coded template signal $u_s(t)$, and
repeat for a plurality of start time differences δ between the second plurality of pulses and the first plurality of pulses and for a plurality of frequency ratios d between the central frequency of the modulated signal within each pulse in the second plurality of pulses and the central frequency of the modulated signal with each corresponding pulse in the first plurality of pulses, the correlating between the template signal and the detected signal to yield, for each start time difference δ and for each frequency ratio d, a correlated signal for each receiver Ri denoted as M(Ri, t), which contains emulated micro-seismic events generated by non-linear interaction at specific mixing locations according to selection rules of non-linear interaction.

29. The system according to claim 28, wherein the processor is configured to calculate, for each start time difference δ and for each frequency ratio d and the corresponding correlated signal M(Ri, t), the spatial coordinates of emulated micro-seismic events where the two acoustic signals interact non-linearly using locus analysis and travel time calculations based on a velocity model for compression or shear wave velocity.

30. The system according to claim 28, wherein the processor is configured to apply time reversal operations to propagate backward in time the signals of the emulated micro-seismic events to the time and location of origination of the micro-seismic events with a propagation velocity model.

31. The system according to claim 30, wherein the processor is configured to determine relative strengths of the micro-seismic events at the locations of origination, wherein the relative strengths at the locations of origination are proportional to non-linear properties of the medium at the locations of origination of the micro-seismic events.

32. The system according to claim 30, wherein the processor is configured to generate a three-dimensional image of the micro-seismic events or the non-linear properties of the medium, or both, by using Kirchhoff imaging, beam imaging, wave equation imaging, or time reversal method from the correlated signals containing emulated micro-seismic events at the mixing zones of the first and second acoustic signals, wherein the correlated signals are obtained from signals received at a plurality of receivers, wherein the first source and the second source are located at different locations.

33. The system according to claim 30, wherein the processor is configured to control the first source and the second source to repeat the generating of the first signal by the first source a plurality of time by disposing the first source at a plurality of locations and repeat the generating of the second signal by the second source a plurality of time by disposing the second source at a plurality of locations; repeat the receiving of the third signal a plurality of time by disposing the receiver at a plurality of locations; and generate multiple three dimensional images of the non-linear properties of the medium by using Kirchhoff imaging, beam imaging, wave equation imaging, or time reversal method from the correlated signals containing emulated micro-seismic events at the mixing zones of the first and second acoustic signals, wherein the correlated signals are obtained from signals received at a plurality of receivers.

34. The system according to claim 33, wherein the processor is configured to update the propagation velocity model by velocity tomography method to minimize the differences in the multiple three dimensional images from received signals from a plurality of locations of the first acoustic source and the second acoustic source.

35. The system according to claim 34, wherein the processor is configured to update the propagation velocity model and to perform imaging iteratively until the differences between the obtained multiple images are minimized and combining the multiple images to create a final three dimensional image of non-linear properties of the medium or the local velocity ratio Vp/Vs or both.

* * * * *